United States Patent [19]

Bernardon et al.

[11] Patent Number: 5,688,817
[45] Date of Patent: Nov. 18, 1997

[54] DI(AROMATIC) COMPOUNDS AND THEIR USE IN HUMAN AND VETERINARY MEDICINE AND IN COSMETICS

[75] Inventors: Jean-Michel Bernardon, Nice; William Robert Pilgrim, Valbonne, both of France

[73] Assignee: Centre Int'l. De Recherches Dermatologiques Galderma, Valbonne, France

[21] Appl. No.: 430,612

[22] Filed: Apr. 28, 1995

Related U.S. Application Data

[62] Division of Ser. No. 167,145, Dec. 16, 1993, Pat. No. 5,439,925, which is a division of Ser. No. 859,522, Aug. 4, 1992, Pat. No. 5,387,594.

[30] Foreign Application Priority Data

Oct. 12, 1990 [LU] Luxembourg ................ 87821

[51] Int. Cl.$^6$ ............... A61K 31/265; A61K 31/325
[52] U.S. Cl. .................. 514/346; 424/401; 424/428; 514/350; 514/352; 514/445; 514/447; 514/471; 514/472; 514/473; 514/480; 514/488; 514/512; 514/859; 514/861; 514/863; 546/292; 546/298; 546/305; 546/309; 549/64; 549/69; 549/479; 549/480; 558/234; 558/274; 560/27; 560/28; 560/29; 560/31; 560/32
[58] Field of Search ................ 546/292, 298, 546/305, 309; 549/64, 69, 479, 480; 558/234, 274; 560/27, 28, 29, 31, 32; 514/346, 350, 352, 445, 447, 471, 472, 473, 480, 488, 512; 424/401, 428

[56] References Cited

U.S. PATENT DOCUMENTS

| | | | |
|---|---|---|---|
| 4,069,343 | 1/1978 | Sellstedt et al. | 560/47 |
| 4,219,625 | 8/1980 | Mares et al. | 525/5 |
| 4,354,033 | 10/1982 | Bhanumati et al. | 560/46 |
| 4,447,624 | 5/1984 | Krutak et al. | 549/69 |
| 4,457,924 | 7/1984 | Jasys et al. | 424/226 |
| 4,895,868 | 1/1990 | Chandraratna | 514/332 |
| 5,037,825 | 8/1991 | Klaus et al. | 514/443 |
| 5,087,743 | 2/1992 | Janssen et al. | 560/48 |
| 5,128,479 | 7/1992 | Janssen et al. | 560/48 |
| 5,258,510 | 11/1993 | Ogawa et al. | 540/476 |
| 5,321,027 | 6/1994 | Ferrini et al. | 514/255 |

FOREIGN PATENT DOCUMENTS

3903988  8/1990  Germany .

OTHER PUBLICATIONS

Ogawa et al., Chemical Abstracts, vol. 116, 128686, 1992.
Nakaguchi et al., Chemical Abstracts, vol. 103, 215181, 1985.
Takahashi et al., Chemical Abstracts, vol. 102, 148897, 1985.
Winkelmann et al., Chemical Abstracts, vol. 96, 68644, 1982.
Johnson, Chemical Abstracts, vol. 83, 188903, 1975.
Hsiao et al., Chemical Abstracts, vol. 79, 49088, 1973.
Bardos et al., Chemical Abstracts, vol. 73, 54283, 1970.
Oku et al., Chemical Abstracts, vol. 123, 285807, 1995.
Akimoto et al., Chemical Abstracts, vol. 119, 8798, 1993.
Ferrini et al., Chemical Abstracts, vol. 117, 131227, 1992.
Hormi et al., Chemical Abstracts, vol. 115, 135902j, 1991.
Kagechika, "Retinobenzoic Acid, 1. Structure–Activity Relationships of Aromatic Amides with Retinoidal Activity", Chemical Abstract, vol. 110, No. 3, 1989, Abstract No. 23483p.
Kagechika, "Retinobenzoic Acid, 4. Conformation of Aromatic Amides with Retinoidal Activity, Importance of Trans–Amide Structure for the Activity", Chemical Abstracts, vol. 111, No. 15, 1989, Abstract No. 134547c.
Okumura et al, Chemical Abstracts, vol. 53 (1959) 17958.
Sekiya et al, Chemical Abstracts, vol. 69 (1968) 43633a.
Raj et al, Chemical Abstracts, vol. 106 (1987) 47103h.
Jogia et al, Chemical Abstracts, vol. 104 (1985) 5715.

*Primary Examiner*—Richard L. Raymond
*Attorney, Agent, or Firm*—Nixon & Vanderhye, P.C.

[57] ABSTRACT

Di(aromatic) compounds corresponding to the following formula:

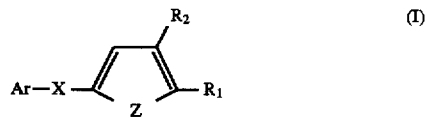

(I)

in which:

Ar represents either

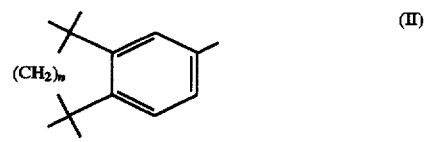

(II)

n=1 or 2 or:

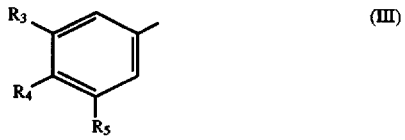

(III)

X represents a divalent radical,
Z represents O, S or a divalent radical, and $R_1$, $R_2$, $R_3$, $R_4$ and $R_5$ represent a hydrogen atom or various organic radicals, and the salts of the compounds of formula (I) when $R_1$ is a carboxylic acid function.

Use in human and veterinary medicine and in cosmetics.

20 Claims, No Drawings

DI(AROMATIC) COMPOUNDS AND THEIR USE IN HUMAN AND VETERINARY MEDICINE AND IN COSMETICS

This is a division of application Ser. No. 08/167,145, filed Dec. 16, 1993, now U.S. Pat. No. 5,439,925, which is a division of application Ser. No. 07/859,522, filed Aug. 4, 1992, now U.S. Pat. No. 5,387,594.

The present invention relates to new di(aromatic) compounds, to a process for preparing them and to their use in human and veterinary medicine and in cosmetics.

These new di(aromatic) compounds find application in the topical and systemic treatment of dermatological conditions linked to a disorder of Keratinization (differentiation/ proliferation) and dermatological or other conditions having inflammatory and/or immunoallergic components, and in degenerative diseases of connective tissue, and possess antitumour activity. In addition, these compounds may be used in the treatment of atopy, both cutaneous and respiratory, and of rheumatoid psoriasis.

They also find application in the ophthalmological field, in particular in the treatment of corneopathies.

The di(aromatic) compounds according to the invention may be represented by the following general formula:

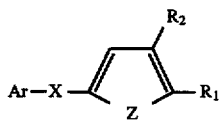
(I)

in which:

Ar represents either a radical

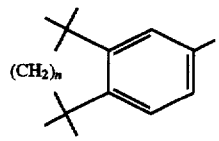
(II)

with n=1 or 2 or a radical

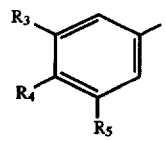
(III)

$R_3$ and $R_5$ representing a hydrogen atom, an OH group, an alkoxy radical having from 1 to 6 carbon atoms, an α-substituted alkyl radical having from 3 to 12 carbon atoms or an α,α-disubstituted alkyl radical having from 4 to 12 carbon atoms, a cycloalkyl radical having from 3 to 12 carbon atoms or a mono- or polycyclic cycloalkyl radical having from 5 to 12 carbon atoms in which the carbon having the free valence is trisubstituted, $R^4$ representing a hydrogen atom, an OH group, an alkoxy radical having from 1 to 6 carbon atoms, an α-substituted alkyl radical having from 3 to 12 carbon atoms, an α,α-disubstituted alkyl radical having from 4 to 12 carbon atoms, a cycloalkyl radical having from 3 to 12 carbon atoms, a mono- or poly-cyclic cycloalkyl radical having from 5 to 12 carbon atoms in which the carbon having the free valence is trisubstituted, a monohydroxyalkyl radical, a polyhydroxyalkyl radical, a fluorine atom, a chlorine atom, an SH group, a group $SR_6$, a group $SOR_6$, a group $SO_2R_6$, an alkenyl radical having from 2 to 6 carbon atoms or an alkenyloxy radical having from 2 to 6 carbon atoms, $R_6$ representing a lower alkyl radical, $R_1$ represents a hydrogen atom, an OH group, a —$CH_3$ radical, a —$CH_2OH$ radical, a radical —$COR_7$, a —$CH(OH)CH_3$ radical, a radical —$CH_2OCOR_8$, a radical —$SO_2R_9$, a radical —$SOR_9$ or a radical —$SR_9$, $R_7$ representing a hydrogen atom, an OH group, a radical —$OR_{10}$, a radical —N(r'r"), a lower alkyl radical, a monohydroxyalkyl radical, a polyhydroxyalkyl radical or a sugar residue, $R_{10}$ representing an alkyl radical having from 1 to 12 carbon atoms or an alkenyl radical having from 2 to 12 carbon atoms, r' and r", which may be identical or different, representing a hydrogen atom, a lower alkyl radical, an aryl radical, an aralkyl radical, an amino acid residue, a sugar residue, an amino sugar residue or a heterocycle, or r' and r" taken together form a heterocycle, $R_8$ representing a saturated or unsaturated, linear or branched alkyl radical having from 1 to 20 carbon atoms or a sugar residue, $R_9$ representing an OH group, a lower alkyl radical or a radical —N(r'r"), $R_2$ represents a hydrogen atom, an OH group, a lower alkyl radical, an alkoxy radical having from 1 to 6 carbon atoms, a fluorine atom, a chlorine atom, a $CF_3$ group, a group $COR_7$, a $CH_2OH$ group or a group $CH_2OR_6$, Z represents an oxygen or sulphur atom, a divalent radical —$CH=CR_{11}$—, a divalent radical —$N=CH$— or a divalent radical —$N=CR_6$—, $R_{11}$ representing a hydrogen atom, an OH group, a lower alkyl radical, an alkoxy radical having from 1 to 6 carbon atoms, a fluorine atom, a chlorine atom or a $CF_3$ group, X is a divalent radical which can be read from left to right or vice versa, selected from the group consisting of:

(i)

R' representing a hydrogen atom or a —$CH_3$ radical,
W representing an oxygen or sulphur atom or a group —NR',
Y representing an oxygen atom or alternatively a sulphur atom when W represents a group —NR',

(ii)

Q representing an oxygen atom or —NR',
Y representing an oxygen atom or alternatively a sulphur atom when Q represents a group —NR',

(iii)

(iv)

R" representing a hydrogen atom, a —$CH_3$ radical, an OH group, a fluorine atom or a chlorine atom, or R' and R" taken together form a methano radical (=$CH_2$) or an oxo radical (=O),

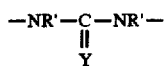

Y representing an oxygen atom or a sulphur atom, with the proviso that, when simultaneously X represents

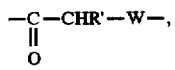

Z represents —CH═CH— and $R_2$ represents a hydrogen atom, when Ar represents a radical of formula (III) in which $R_3$ and $R_5$ are other than a hydrogen atom and other than an α-substituted or α,α-disubstituted alkyl radical having from 3 to 5 carbon atoms, and the salts of the compounds of formula (I) when $R_1$ represents a carboxylic acid function, and the optical isomers of the said compounds of formula (I).

When the compounds according to the invention take the form of salts, the latter are then alkali metal or alkaline earth metal or alternatively zinc salts or salts of an organic amine.

Lower alkyl radical is understood to mean a radical having from 1 to 6 carbon atoms, and preferably methyl, ethyl, isopropyl, butyl and tert-butyl radicals.

Alkoxy radical having from 1 to 6 carbon atoms should be understood to mean a methoxy, ethoxy, isopropoxy or butoxy radical.

α-Substituted alkyl radical having from 3 to 12 carbon atoms should be understood, in particular, to mean an isopropyl, 1-methylpropyl or 1-ethylpropyl radical.

α,α-Disubstituted alkyl radical having from 4 to 12 carbon atoms should be understood, in particular, to mean a tert-butyl, 1,1-dimethylpropyl, 1-methyl-1-ethylpropyl, 1-methyl-1-ethylhexyl or 1,1-dimethyldecyl radical.

Monohydroxyalkyl radical should be understood to mean a radical having from 1 to 6 carbon atoms, in particular a 2-hydroxyethyl, 2-hydroxypropyl or 3-hydroxypropyl radical.

Polyhydroxyalkyl radical should be understood to mean a radical containing from 2 to 6 carbon atoms and from 2 to 5 hydroxyl groups, such as 2,3-dihydroxypropyl, 2,3,4-trihydroxybutyl and 2,3,4,5-tetrahydroxypentyl radicals or the pentaerythritol residue.

Aryl radical should be understood to mean a phenyl radical optionally substituted with at least one halogen atom, one hydroxyl or one nitro function.

Aralkyl radical should be understood to mean a benzyl or phenethyl radical optionally substituted with at least one halogen atom, one hydroxyl or one nitro function.

Cycloalkyl radical having from 3 to 12 carbon atoms should be understood to mean, in particular, a cyclopentyl or cyclohexyl radical.

Mono- or polycyclic cycloalkyl radical having from 5 to 12 carbon atoms in which the carbon having the free valence is trisubstituted should be understood to mean a 1-methylcyclohexyl or 1-adamantyl radical.

Alkenyloxy radical having from 2 to 6 carbon atoms should be understood to mean linear or branched, and in particular allyloxy and vinyloxy, radicals.

Alkenyl radical having from 2 to 6 carbon atoms should be understood, in particular, to mean vinyl, allyl or 2-butenyl radicals.

When $R_{10}$ represents an alkyl radical having from 1 to 12 carbon atoms or an alkenyl radical having from 2 to 12 carbon atoms, these radicals should be understood to mean linear or branched radicals optionally substituted with one or more hydroxyl groups or one or more fluorine atoms.

Amino acid residue should be understood to mean a residue derived, for example, from one of the 20 amino acids of L or D configuration (or a racemic mixture thereof) of which mammalian proteins are composed.

Sugar residue should be understood to mean a residue derived, for example, from glucose, galactose or mannose.

Amino sugar residue should be understood to mean a residue derived, for example, from glucosamine, galactosamine or mannosamine.

Heterocycle should preferably be understood to mean a piporidino, morpholino, pyrrolidino or piperazino radical, optionally substituted at the 4-position with a $C_1$-$C_6$ alkyl or a mono- or polyhydroxyalkyl radical such as are defined above.

Among the compounds of formula (I) above, the following may be mentioned in particular:

4-(5,6,7,8-Tetrahydro-5,5,8,8-tetramethyl-2-naphthylglyoxyloyloxy)benzoic acid, 4-(5,6,7,8-Tetrahydro-5,5,8,8-tetramethyl-2-naphthylacetoxy)benzoic acid, 4-(5,6,7,8-Tetrahydro-5,5,8,8-tetramethyl-2-naphthylacetamido)benzoic acid, 4-(α-Methylene-5,6,7,8-tetrahydro-5,5,8,8-tetramethyl-2-naphthylacetoxy)benzoic acid, 4-(5,6,7,8-Tetrahydro-5,5,8,8-tetramethyl-2-naphthoyloxymethyl)benzoic acid, 4-(5,6,7,8-Tetrahydro-5,5,8,8-tetramethyl-2-naphthoylthiomethyl)benzoic acid, 4-(5,6,7,8-Tetrahydro-5,5,8,8-tetramethyl-2-naphthylcarboxamidomethyl)benzoic acid, 4-(N-Methyl-5,6,7,8-tetrahydro-5,5,8,8-tetramethyl-2-naphthylcarboxamidomethyl)benzoic acid, 4-(5,6,7,8-Tetrahydro-5,5,8,8-tetramethyl-2-naphthylmethyloxycarbonyl)benzoic acid, 4-[(5,6,7,8-Tetrahydro-5,5,8,8-tetramethyl-2-naphthylmethylthio)carbonyl]benzoic acid, 5-(5,6,7,8-Tetrahydro-5,5,8,8-tetramethyl-2-naphthoyloxymethyl)-2-thiophenecarboxylic acid, 4-(5,6,7,8-Tetrahydro-5,5,8,8-tetramethyl-2-naphthyloxycarboxamido)benzoic acid, 4-[5,6,7,8-Tetrahydro-5,5,8,8-tetramethyl-2-naphthyl(carbonyldioxy)]benzoic acid, 4-[1-(5,6,7,8-Tetrahydro-5,5,8,8-tetramethyl-2-naphthoyloxy)ethyl]benzoic acid, 4-{[1-(5,6,7,8-Tetrahydro-5,5,8,8-tetramethyl-2-naphthyl)ethyloxy]carbonyl}benzoic acid, 4-(3,5-Di-tert-butyl-4-hydroxybenzoyloxymethyl)benzoic acid, 4-[3-(1-Adamantyl)-4-methoxybenzoyloxymethyl]benzoic acid, 4-(3-tert-Butyl-4-methoxybenzoyloxymethyl)benzoic acid, 4-(4-tert-Butylbenzoyloxymethyl)benzoic acid, 4-[4-(1-Adamantyl)-3-methoxybenzoyloxymethyl]benzoic acid, 4-[3-(1-Adamantyl)-4-methoxyphenoxycarboxamido]benzoic acid, 4-[3-(1-Adamantyl)-4-methoxyphenyl(carbonyldioxy)]benzoic acid, 4-[3-(1-Adamantyl)-4-methoxyphenylacetamido]benzoic acid, 4-(5,6,7,8-Tetrahydro-5,5,8,8-tetramethyl-2-naphthoylformamido)benzoic acid, 4-(α-Hydroxy-5,6,7,8-tetrahydro-5,5,8,8-tetramethyl-2-naphthylacetamido)benzoic acid, 4-(5,6,7,8-Tetrahydro-5,5,8,8-tetramethyl-2-naphthylcarbamoylmethyl)benzoic acid, 2-Hydroxy-4-(5,6,7,8-tetrahydro-5,5,8,8-tetramethyl-2-naphthylacetoxy)benzoic acid, 4-(5,6,7,8-Tetrahydro-5,5,8,8-tetramethyl-2-naphthyloxycarbonylmethyl)benzoic acid, 4-(N-Methyl-5,6,7,8-tetrahydro-5,5,8,8-tetramethyl-2-naphthylacetamido)benzoic acid, 4-(α-Fluoro-5,6,7,8-tetrahydro-5,5,8,8-tetramethyl-2-naphthylacetamido)benzoic acid, 4-[3-(1-Adamantyl)-4-methoxyphenylureido]benzoic acid, 2-Hydroxy-4-(5,6,7,8-tetrahydro-5,5,8,8-tetramethyl-2-naphthoylmethyloxy)benzoic acid, and 4-[2-(5,6,7,8-Tetrahydro-5,5,8,8-tetramethyl-2-naphthyl) propionamido]benzoic acid.

Various reaction schemes may be envisaged for obtaining the compounds of the formula (I) in the case where Y is an oxygen atom.

The following reaction schemes may be mentioned:

In the case where X is either (i) or (iv)

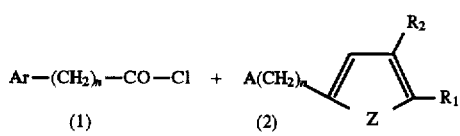

(1)  (2)

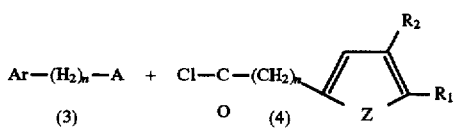

(3)  (4)

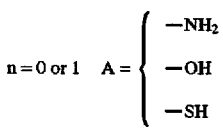

n = 0 or 1   A = { —NH₂, —OH, —SH }

The main step in this preparation consists in reacting, in an anhydrous medium, in an organic solvent such as tetrahydrofuran or methylene chloride containing a tertiary amine (triethylamine) or pyridine or an alkali metal hydride (sodium hydride), an activated form of a substituted aromatic acid or of a substituted arylacetic acid, for example an acid chloride (1) or (4) or a mixed anhydride, with an aromatic compound bearing a hydroxyl or amino or thiol function (2) or (3), the reaction being performed at room temperature and with stirring.

When R₁ represents a —COOH radical, the compounds are prepared by protecting R₁ with a protective group of the allyl, benzyl or tert-butyl type.

Conversion to the free form may be performed:

in the case of an allyl protective group, by means of a catalyst such as certain transition metal complexes in the presence of a secondary amine, in the case of a benzyl protective group, by debenzylation in the presence of hydrogen by means of a catalyst such as palladium on charcoal, in the case of a tert-butyl protective group, by means of trimethylsilyl iodide.

In the case where X is either (ii) or (v)

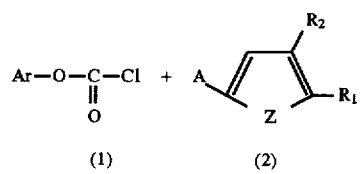

(1)  (2)

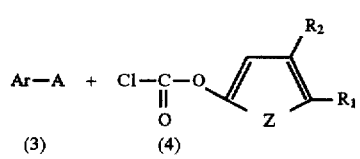

(3)  (4)

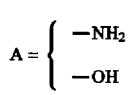

A = { —NH₂, —OH }

The main step in this preparation consists in reacting, in an anhydrous medium, in an organic solvent such as methylene chloride containing a tertiary amine (triethylamine) or pyridine, a chloroformate (1) or (4), prepared, for example, from a hydroxyaryl derivative and trichloromethyl chloroformate or phosgene, with an aromatic compound bearing a hydroxyl or amino function (2) or (3), the reaction being performed at room temperature and with stirring.

In the case where Rx represents a —COOH radical, compounds are preferably prepared by protecting R₁ with a benzyl protective group. Conversion to the free form is then performed by debenzylation in the presence of hydrogen by means of a catalyst such as palladium on charcoal.

In the case where X is (iii) and if Z is not an oxygen atom,

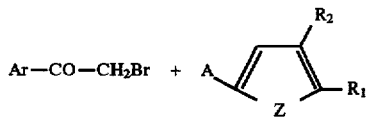

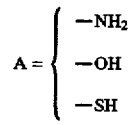 A = { —NH₂, —OH, —SH }

The main step in this preparation consists in reacting, in the presence of potassium carbonate or an alkali metal hydride (sodium hydride), or by phase transfer using, for example, tetrabutylammonium bromide as a quaternary ammonium salt, an aromatic alpha-bromo ketone with an aromatic compound bearing a hydroxyl or amino or thiol function in the paraposition with respect to the radical R₁.

In the case where R₁ represents a —COOH radical, the compounds are preferably prepared by protecting R₁ with an allyl protective group. Conversion to the free form is performed by means of a catalyst such as tetrakis (triphenylphosphine)palladium(0) in the presence of a secondary amine (morpholine).

The acids thereby obtained maybe converted in a known manner to the corresponding acid chloride which, when treated with an alcohol (R₆OH) or an amine HN(r')(r"), gives the corresponding ester or amide.

The subject of the present invention is also the compounds of formula (I), as defined above, by way of a medicinal product.

The compounds according to the invention exhibit good stability to light and to oxygen.

These compounds exhibit good activity in the test of differentiation of mouse embryonic teratocarcinoma cells (F9) (Cancer Research 43, p. 5268, 1983) and/or in the test of ornithine decarbexylase inhibition after induction by "tape stripping" in nude rats (Lab. Animals 21, p. 233–240, 1987) or by TPA in mice (Cancer Research 38, p. 793–801, 1978). These tests show the activities of the compounds in the fields of differentiation and of proliferation, respectively.

The compounds according to the invention are especially well suited to the following areas of treatment:

1) For treating dermatological conditions linked to a disorder of Keratinization involving differentiation and proliferation, in particular for treating acne vulgaris, comedonic or polymorphic acne, nodulocystic acne, acne conglobata, senile acne and secondary acnes such as solar, drug and occupational acne.

2) For treating other types of disorder of keratinization, in particular ichthyoses, ichthyosiform states, Darier's disease, palmoplantar keratoderma, leucoplakia and leucoplakiform states, and lichen.

3) For treating other dermatological conditions linked to a disorder of Keratinization with an inflammatory and/ or immunoallergic component, and in particular all forms of psoriasis, whether cutaneous, mucosal or ungual, and even psoriatic rheumatism, or alternatively cutaneous atopy, such as eczema, or respiratory atopy; the compounds may also be used in some inflammatory conditions not entailing a disorder of Keratinization.

4) For treating all dermal or epidermal proliferations, whether benign or malignant, including those of viral origin such as common warts, flat warts and epidermodysplasia verruciformis, it also being possible for the proliferations to be induced by ultraviolet light, in particular in the case of basal cell and prickle cell epithelioma.

5) For treating other dermatological disorders such as vesicular dermatoses and collagen diseases.

6) For treating certain ophthaimological disorders, in particular corneopathies.

7) For compensating for or combating skin ageing, both light-induced and that occurring with the passage of time.

8) For preventing or treating the stigmata of epidermal and/or dermal atrophy induced by local or systemic corticosteroids, or any other form of cutaneous atrophy.

9) For promoting cicatrisation.

10) For combating disorders of sebaceous function, such as seborrhoea of acne or simple seborrhoea.

The subject of the present invention is also medicinal compositions containing at least one compound of formula (I) as defined above or one of its salts.

The subject of the present invention is hence also a new medicinal composition intended, in particular, for the treatment of the abovementioned conditions, characterized in that it contains at least one compound of formula (I) and/or one of its salts in a pharmaceutically acceptable vehicle.

The compounds according to the invention are generally administered at a daily dose of approximately 0.1 mg/kg to 100 mg/kg of body weight.

The administration may be performed enterally, parenterally, topically or via the eye. For enteral administration, the medicinal products can take the form of tablets, hard gelatin capsules, dragees syrups, suspensions, solutions, powders, granules or emulsions. For parenteral administration, the compositions can take the form of solutions or suspensions for perfusion or for injection.

For topical administration, the pharmaceutical compositions based on the compounds according to the invention are intended for treatment of the skin and the mucosa, and take the form of ointments, creams, milks, salves, powders, impregnated pads, solutions, gels, sprays, lotions or suspensions. They can also take the form of microspheres or nanospheres or lipid or polymeric vesicles or polymeric patches or hydrogels permitting a controlled release.

These compositions for topical administration can take either anhydrous form or aqueous form, depending on the clinical indication.

For ocular administration, they are mainly eye washes.

These compositions contain at least one compound of formula (I) such as defined above or one of its salts, at a concentration preferably of between 0.0001 and 5% relative to the total weight of the composition.

The compounds of formula (I) according to the invention also find application in the cosmetic field, especially in body and hair hygiene, and in particular for the treatment of skin having a tendency to develop acne, for hair regrowth and counteracting hair loss, for combating a greasy appearance of the skin or hair, in protection against the deleterious effects of sunlight or in the treatment of physiologically dry skin.

The present invention hence also relates to a cosmetic composition containing at least one compound of formula (I) or one of its salts in a cosmetically acceptable vehicle, this composition taking the form, in particular, of a cream, a milk, a lotion, a gel, microspheres or nanospheres or lipid or polymeric vesicles, a soap or a shampoo.

The concentration of the compound of formula (I) in the cosmetic compositions is between 0.0001 and 0.1% by weight, and preferably between 0.001 and 0.01% by weight.

The medicinal and cosmetic compositions according to the invention can contain inert or even pharmacodynamically or cosmetically active additives, and in particular: hydrating agents such as thiamorpholinone and its derivatives or urea; antiseberrhoeic or anti-acne agents such as S-carboxymethylcysteine, S-benzylcysteamine, their salts and their derivatives, thioxolone or benzoyl peroxide; antibiotics such as erythromycin and its esters, neomycin, clindamycin and its esters, tetracyclines, and antifungal agents such as ketoconazole or 4,5-polymethylene-3-isothiazolinones; agents promoting hair regrowth, such as "minoxidil" (2,4-diamino-6-piperidinopyrimidine 3-oxide) and its derivatives, diazoxide (7-chloro-3-methyl-1,2,4-benzothiadiazine 1,1-dioxide) and phenytoin (5,5-diphenylimidazolidine-2,4-dione); steroidal and non-steroidal anti-inflammatory agents; carotenoids, and in particular β-carotene; antipsoriatic agents such as anthralin and its derivatives and 5,8,11,14-eicosatetraynoic and 5,8,11-eicosatriynoic acids, their esters and their amides.

The compositions according to the invention can also contain flavors improvers, preservatives such as para-hydroxybenzoic acid esters, stabilisers, moisture regulators, pH regulators, osmotic pressure modifiers, emulsifiers, UV-A and UV-B screening agents and anti-oxidants such as α-tocopherol, butylated hydroxyanisole or butylated hydroxytoluene.

Several examples of preparation of the active compounds of formula (I) according to the invention, as well as examples of compositions containing them, will now be given by way of illustration and without any implied limitation.

PREPARATION EXAMPLES

Example 1

4-(5,6,7,8-Tetahydro-5,5,8,8-tetramethyl-2-naphthylglyoxyloyloxy)benzoic acid (a) Ethyl 5,6,7,8-tetrahydro-5,5,8,8-tetramethyl-2-naphthylglyoxylate 14.5 g (0.109 mol) of aluminium chloride and 100 ml of dichloromethane are introduced into a three-necked flask, a mixture of 11.7 g (62 mmol) of 5,6,7,8-tetrahydro-5,5,8,8-tetramethylnaphthalene and 8 ml (71 mmol) of ethoxallyl chloride in 100 ml of dichloromethane is added dropwise and the mixture is stirred at room temperature for one hour. The reaction medium is poured into water, the mixture is extracted with ethyl ether and the organic phase is separated after settling has taken place, dried over magnesium sulphate and evaporated. The residue obtained is purified by chromatography on a silica column and eluted with a mixture of dichloromethane and hexane (30:70). After evaporation of the solvents, 16.5 g (93%) of the expected ester are collected in the form of a slightly yellow oil.

(b) 5,6,7,8-Tetrahydro-5,5,8,8-tetramethyl-2-naphthylglyoxylic acid 16 g (55.6 mmol) of the ester obtained above in (a) and 50 ml of ethyl alcohol are introduced into a round-bottomed flask. A solution of 2.5 g (58.5 mmol) of sodium hydroxide in 50 ml of water is added and the mixture is heated to reflux for one hour. The reaction medium is evaporated to dryness, the residue is taken up with water, the mixture is extracted with ethyl ether, the aqueous phase is separated after settling has taken place, acidified to pH 1 with concentrated hydrochloric acid and extracted with ethyl ether, and the organic phase is separated after settling has taken place, dried over magnesium sulphate and evaporated. 14 g (97%) of 5,6,7,8-tetrahydro-5,5,8,8-tetramethyl-2-naphthylglyoxylic acid are collected in the form of a colorless oil.

(c) 5,6,7,8-Tetrahydro-5,5,8,8-tetramethyl-2-naphthylglyoxyloyl chloride 2.6 g (10 mmol) of 5,6,7,8-tetrahydro-5,5,8,8-tetramethyl-2-naphthylglyoxylic acid in 50 ml of dichloromethane are introduced into a round-bottomed flask, 2 ml (10 mmol) of dicyclohexylamine are added and the mixture is stirred at room temperature for one hour. 800 µl (10 mmol) of thionyl chloride are then added dropwise and the mixture is stirred at room temperature for one hour. It is evaporated to dryness, the residue is taken up with 200 ml of ethyl ether, the dicyclohexylamine salt is filtered off and the filtrate is evaporated. 2.8 g (100%) of crude acid chloride are obtained, which product is used for the next step of the synthesis without further treatment.

(d) tert-Butyl 4-(5,6,7,8-tetrahydro-5,5,8,8-tetramethyl-2-naphthylglyoxyloyloxy)benzoate 1.94 g (10 mmol) of tert-butyl 4-hydroxybenzoate, 1.4 ml (10 mmol) of triethylamine and 50 ml of THF are introduced into a round-bottomed flask. A solution of 2.8 g (10 mmol) of the acid chloride obtained above in (c) in 50 ml of THF is added dropwise and the mixture is stirred at room temperature for four hours. The reaction medium is poured into water, the mixture is extracted with ethyl ether and the organic phase is separated after settling has taken place, dried over magnesium sulphate and evaporated. The residue obtained is purified by chromatography on a silica column and eluted with a mixture of dichloromethane and hexane (40:60). After evaporation of the solvents, 2 g (46%) of tert-butyl ester are collected in the form of a colorless oil.

(e) 4-(5,6,7,8-Tetrahydro-5,5,8,8-tetramethyl-2-naphthylglyoxyloyloxy)benzoic acid 1.6 g (3.6 mmol) of ester obtained above in (d) and 50 ml of carbon tetrachloride are introduced into a round-bottomed flask. The mixture is cooled in an ice-bath, 520 µl (3.6 mmol) of trimethylsilyl iodide are added dropwise and the mixture is stirred at room temperature for four hours. The reaction medium is poured into water, the mixture is extracted with ethyl ether and the organic phase is separated after settling has taken place, dried over magnesium sulphate and evaporated. The residue obtained is purified by chromatography on a silica column and eluted with a mixture of dichloromethane and hexane (95:5). After evaporation of the solvents, 830 mg (59%) of 4-(5,6,7,8-tetrahydro-5,5,8,8-tetramethyl-2-naphthylglyoxyloyloxy)benzoic acid, melting point 160°–161° C., are collected.

Example 2

4-(5,6,7,8-Tetrahydro-5,5,8,8-tetramethyl-2-naphthylacetoxy)benzoic acid (a) 5,6,7,8-Tetrahydro-5,5,8,8-tetramethyl-2-naphthylacetic acid 4.68 g (18 mmol) of 5,6,7,8-tetrahydro-5,5,8,8-tetramethyl-2-naphthylglyoxylic acid and 50 ml of hydrazine hydrate are introduced into a round-bottomed flask and the mixture is heated to reflux until dissolution has taken place. At 100° C., 8 g of potassium hydroxide are added in small portions and the mixture is heated to reflux for four hours. The reaction medium is evaporated to dryness, the residue is taken up with water, the mixture is acidified to pH 1 with concentrated hydrochloric acid and extracted with ethyl ether, and the organic phase is separated after settling has taken place, then dried over magnesium sulphate and evaporated. The residue obtained is purified by chromatography on a silica column and eluted with a mixture of dichloromethane and ethyl ether (95:5). After evaporation of the solvents, 3.8 g (86%) of 5,6,7,8-tetrahydro-5,5,8,8-tetramethyl-2-naphthylacetic acid, melting point 149°–150° C., are collected.

(b) 5,6,7,8-Tetrahydro-5,5,8,8-tetramethyl-2-naphthylacetyl chloride 6.6 g (26.8 mmol) of 5,6,7,8-tetrahydro-5,5,8,8-tetramethyl-2-naphthylacetic acid and 20 ml of thionyl chloride are heated to reflux until gaseous evolution has ceased. The mixture is evaporated to dryness and 7.1 g (100%) of the crude acid chloride are obtained, which product is used for the next step of the synthesis without further treatment.

(c) Benzyl 4-(5,6,7,8-tetrahydro-5,5,8,8-tetramethyl-2-naphthylacetoxy)benzoate

In a manner similar to Example 1(d), by reaction of 1.93 g (7.7 mmol) of acid chloride obtained above in 2(b) with 1.75 g (7.7 mmol) of benzyl 4-hydroxybenzoate, 2.3 g (65%) of benzyl ester are obtained in the form of a translucent oil.

(d) 4-(5,6,7,8-Tetrahydro-5,5,8,8-tetramethyl-2-naphthylacetoxy)benzoic acid 2.4 g (5.2 mmol) of benzyl 4-(5,6,7,8-tetrahydro-5,5,8,8-tetramethyl-2-naphthylacetoxy)benzoate, 1 g of palladium on charcoal (5%) and 100 ml of dioxane are introduced into a reactor. The mixture is hydrogenated at room temperature and under a pressure of 7 bars for three hours, the catalyst is filtered off and washed with twice 50 ml of THF and the filtrates are evaporated. The residue obtained is ground in the minimum amount of ethyl ether, filtered off and dried. 1.35 g (70%) of 4-(5,6,7,8-tetrahydro-5,5,8,8-tetramethyl-2-naphthylacetoxy)benzoic acid, melting point 142°–143° C., are obtained.

Example 3

4-(5,6,7,8-tetrahydro-5,5,8,8-tetramethyl-2-naphthylacetamido)benzoic acid (a) Allyl 4-aminobenzoate 50 ml of allyl alcohol are introduced into a round-bottomed flask. 750 mg (22 mmol) of sodium are added in small portions and the mixture is stirred until the metal has reacted completely. 30.2 g (0.2 mol) of ethyl 4-aminobenzoate, dissolved in 200 ml of allyl alcohol, are then introduced and the mixture is heated to reflux and distilled until 180 ml of distillate have been obtained. The reaction medium is evaporated, the residue is taken up with water and ethyl ether and the organic phase is separated after settling has taken place, dried over magnesium sulphate and evaporated. The residue obtained is ground in 200 ml of hexane and filtered off. 29 g (82%) of allyl ester, melting point 48°–50° C., are collected.

(b) Allyl 4-(5,6,7,8-tetrahydro-5,5,8,8-tetramethyl-2-naphthylacetamido)benzoate In a manner similar to Example 1(d), by reaction of 4.5 g (16.8 mmol) of 5,6,7,8-tetrahydro-5,5,8,8-tetramethyl-2-naphthylacetyl chloride with 3 g (16.8 mmol) of allyl 4-aminobenzoate, 5.1 g (75%) of the expected ester are obtained in the form of a slightly yellow oil.

(c) 4-(5,6,7,8-Tetrahydro-5,5,8,8-tetramethyl-2-naphthylacetamido)benzoic acid 2.15 g (5.3 mmol) of the ester obtained above in (b), 346 mg (0.3 mmol) of tetrakis(triphenylphosphine)palladium(O) and 50 ml of anhydrous THF are introduced under a stream of nitrogen into a three-necked flask. 4.6 ml (53 mmol) of morpholine are added dropwise and the mixture is stirred at room temperature for four hours. The reaction medium is evaporated to dryness, the residue is ground in ethyl ether and the morpholine salt formed is then filtered off. The salt is introduced into 100 ml of water, the mixture is acidified to pH 1 with concentrated hydrochloric acid and extracted with ethyl ether and the organic phase is separated after settling has taken place, then dried over magnesium sulphate and evaporated. The residue obtained is purified by chromatography on a silica column and eluted with a mixture of dichloromethane and ethyl ether (95:5). After evaporation of the solvents, 1.5 g (79%) of 4-(5,6,7,8-tetrahydro-5,5,8,8-tetramethyl-2-naphthylacetamido)benzoic acid, melting point 203°–204° C., are collected.

Example 4

4-(α-Methylene-5,6,7,8-tetrahydro-5,5,8,8-tetramethyl-2-naphthylacetoxy)benzoic acid (a) α-Hydroxy-α-methyl-5,6,7,8-tetrahydro-5,5,8,8-tetramethyl-2-naphthylacetic acid 3.1 g (12 mmol) of 5,6,7,8-tetrahydro-5,5,8,8-tetramethyl-2-naphthylglyoxylic acid and 50 ml of THF are introduced into a three-necked flask. At 0° C. and under a stream of nitrogen, 16 ml (48 mmol) of a solution of ethylmagnesium iodide in ethyl ether (3M) are added dropwise and the mixture is stirred at room temperature for four hours. The reaction medium is poured into water, the mixture is extracted with ethyl ether and the organic phase is separated after settling has taken place, then dried over magnesium sulphate and evaporated. The residue obtained is purified by chromatography on a silica column and eluted with a mixture of dichloromethane and ethyl ether (20:80). After evaporation of the solvents, 2.6 g (79%) of the expected product, melting point 168°–169° C., are collected.

(b) α-Methylene-5,6,7,8-tetrahydro-5,5,8,8-tetramethyl-2-naphthylacetic acid 4.4 ml of concentrated hydrochloric acid are added to 2.4 g (8.7 mmol) of the acid obtained above in (a) in 80 ml of dioxane and the mixture is heated to reflux for four hours. The reaction medium is evaporated to dryness, the residue is taken up with water and ethyl ether and the organic phase is separated after settling has taken place, then dried over magnesium sulphate and evaporated. The residue obtained is purified by chromatography on a silica column, eluting with ethyl ether. 2 g (91%) of the expected acid, melting point 149°–150° C., are collected.

(c) tert-Butyl α-methylene-5,6,7,8-tetrahydro-5,5,8,8-tetramethyl-2-naphthylacetoxybenzoate 1.9 g (7.3 mmol) of acid obtained above in (b), 1.5 g (7.3 mmol) of tert-butyl 4-hydroxybenzoate and 100 ml of THF are introduced into a round-bottomed flask. 1.5 g (7.3 mmol) of N,N'-dicyclohexylcarbodiimide and 0.9 g (7.3 mmol) of 4-dimethylaminopyridine are added successively and the mixture is stirred at room temperature for four hours. The reaction medium is poured into water, the mixture is extracted with ethyl ether and the organic phase is separated after settling has taken place, dried over magnesium sulphate and evaporated. The residue obtained is purified by chromatography on a silica column, eluting with dichloromethane. 2.3 g (73%) of the expected ester are collected in the form of a colorless oil.

(d) 4-(α-Methylene-5,6,7,8-tetrahydro-5,5,8,8-tetramethyl-2-naphthylacetoxy)benzoic acid In a manner similar to Example 1(e), starting with 2.1 g (4.8 mmol) of the ester obtained above in (c), 1.7 g (95%) of the expected acid, melting point 186°–187° C., are obtained.

Example 5

4-(5,6,7,8-Tetrahydro-5,5,8,8-tetramethyl-2-naphthoyloxymethyl)benzoic acid (a) Benzyl 4-formylbenzoate 1.8 g (60 mmol) of sodium hydride (80% in oil) and 50 ml of DMF are introduced under a stream of nitrogen into a round-bottomed flask. 7.5 g (50 mmol) of 4-formylbenzoic acid, dissolved in 100 ml of DMF, are added dropwise and the mixture is stirred at room temperature until gaseous evolution has ceased. A solution of 7.1 ml (60 mmol) of benzyl bromide in 50 ml of DMF is then introduced dropwise and the mixture is stirred at room temperature for four hours. The reaction medium is poured into water, the mixture is extracted with ethyl ether and the organic phase is separated after settling has taken place, dried over magnesium sulphate and evaporated. The residue obtained is purified by chromatography on a silica column and eluted with a mixture of dichloromethane and hexane (50:50). After evaporation of the solvents, 10.9 g (91%) of the expected benzyl ester are collected in the form of a colorless oil.

(b) Benzyl hydroxymethylbenzoate 10.3 g (43 mmol) of benzyl 4-formylbenzoate, 50 ml of THF and 50 ml of methyl alcohol are introduced into a round-bottomed flask. While cooling in an icebath, 820 mg (21.5 mmol) of sodium borohydride are added in small portions and the mixture is stirred at room temperature for two hours. The reaction medium is poured into water, the mixture is extracted with ethyl ether and the organic phase is separated after settling has taken place, dried over magnesium sulphate and evaporated. 10.4 g (100%) of the expected product, melting point 55°–56° C., are collected.

(c) Benzyl 4-(5,6,7,8-tetrahydro-5,5,8,8-tetramethyl-2-naphthoyloxymethyl)benzoate In a manner similar to Example 1(d), by reaction of 2.78 g (10 mmol) of 5,6,7,8-tetrahydro-5,5,8,8-tetramethyl-2-naphthoyl chloride with 2.42 g (10 mmol) of benzyl 4-hydroxybenzoate, 3.7 g (81%) of benzyl ester are obtained in the form of a colorless oil.

(d) 4-(5,6,7,8-Tetrahydro-5,5,8,8-tetramethyl-2-naphthoyloxymethyl)benzoic acid

In a manner similar to Example 2(d), starting with 2.2 g (4.8 mmol) of the ester obtained above in (c), 800 mg (46%) of 4-(5,6,7,8-tetrahydro-5,5,8,8-tetramethyl-2-naphthoyloxymethyl)benzoic acid, melting point 176°–177° C., are obtained.

Example 6

4-(3,5-Di-tert-butyl-4-hydroxybenzoyloxymethyl)benzoic acid (a) Benzyl 4-(3,5-di-tert-butyl-4-hydroxybenzoyloxymethyl)benzoate acid In a manner similar to Example 1(d), by reaction of 2.33 g (10 mmol) of 3,5-di-tert-butyl-4-hydroxybenzoyl chloride with 2.42 g (10 mmol) of benzyl 4-hydroxybenzoate, 2.9 g (61%) of benzyl ester, melting point 110°–111° C., are obtained.

(b) 4-(3,5-Di-tert-butyl-4-hydroxybenzoyloxymethyl)benzoic acid

In a manner similar to Example 2(d), starting with 1.4 g (3.1 mmol) of the ester obtained above in (a), 535 mg (45%) of 4-(3,5-di-tert-butyl-4-hydroxybenzoyloxymethyl)benzoic acid, melting point 171°–172° C., are obtained.

Example 7

4-[3-(1-Adamantyl)-4-methoxybenzoyloxymethyl]benzoic acid (a) Allyl 4-formylbenzoate 3.3 g (0.11 mol) of sodium hydride (80% in oil) and 100 ml of DMF are introduced under a stream of nitrogen into a round-bottomed flask. 15 g (0.1 mol) of 4-formylbenzoic acid, dissolved in 200 ml of DMF are added dropwise and the mixture is stirred at room temperature until gaseous evolution has ceased. 9.5 ml (0.11 mol) of allyl bromide are then introduced and the mixture is stirred at room temperature for four hours. The reaction medium is poured into water, the mixture is extracted with ethyl ether and the organic phase is separated after settling has taken place, then dried over magnesium sulphate and evaporated. 19 g (100%) of allyl ester are collected in the form of a slightly yellow oil.

(b) Allyl 4-hydroxymethylbenzoate

In a manner similar to Example 5(b), starting with 17.3 g (91 mmol) of allyl 4-formylbenzoate, 15.1 g (86%) of the expected product are obtained in the form of a colorless oil.

(c) Allyl 4-[3-(1-adamantyl)-4-methoxybenzoyloxymethyl]benzoate

In a manner similar to Example 1(d), by reaction of 3.1 g (10 mmol) of 3-(1-adamantyl)-4-methoxybenzoyl chloride with 1.92 g (10 mmol) of allyl 4-hydroxybenzoate, 2.9 g (63%) of allyl ester are obtained in the form of a colorless oil.

(d) 4-[3-(1-Adamantyl)-4-methoxybenzoyloxymethyl]benzoic acid

In a manner similar to Example 3(c), starting with 2.8 g (6.1 mmol) of the ester obtained above in (c), 1.6 g (62%) of 4-[3-(1-adamantyl)-4-methoxybenzoyloxymethyl]benzoic acid, melting point 215°–216° C., are obtained.

Example 8

4-(3-tert-butyl-4-methoxybenzoyloxymethyl)benzoic acid (a) Allyl 4-(3-tert-butyl-4-methoxybenzoyloxymethyl)benzoate In a manner similar to Example 1(d), by reaction of 2.4 g (18 mmol) of 3-tert-butyl-4-methoxybenzoyl chloride with 1.9 g (10 mmol) of allyl 4-hydroxymethylbenzoate, 2.65 g (69%) of allyl ester are obtained in the form of a slightly yellow oil.

(b) 4-(3-tert-Butyl-4-methoxybenzoyloxymethyl)benzoic acid

In a manner similar to Example 3(c), starting with 2.65 g (7 mmol) of the ester obtained above in (a), 1.55 g (64%) of 4-(3-tert-butyl-4-methoxybenzoyloxymethyl)benzoic acid, melting point 171°–172° C., are obtained.

Example 9

4-(4-tert-Butylbenzoyloxymethyl)benzoic acid (a) Allyl 4-(4-tert-butylbenzoyloxymethyl)benzoate In a manner similar to Example 1(d), by reaction of 2 g (15 mmol) of 4-tert-butylbenzoyl chloride with 2.9 g (15 mmol) of allyl 4-hydroxymethylbenzoate, 4 g (77%) of allyl ester are obtained in the form of a colorless oil.

(b) 4-(4-tert-Butylbenzoyloxymethyl)benzoic acid

In a manner similar to Example 3(c), starting with 3.8 g (10.8 mmol) of the ester obtained above in (a), 3 g (89%) of 4-(4-tert-butylbenzoyloxymethyl)benzoic acid, melting point 153°–154° C., are obtained.

Example 10

4-[4-(1-Adamantyl)-3-methoxybenzoyloxymethyl]benzoic acid (a) 2-(1-Adamantyl)-5-bromophenol 17 g (0.1 mol) of 3-bromophenol, 15.22 g (0.1 mol) of 1-adamantanol and 50 ml of dichloromethane are introduced into a round-bottomed flask. 5 ml of concentrated sulphuric acid are added dropwise and the mixture is stirred at room temperature for 24 hours. The reaction medium is poured into water, the mixture is neutralized with sodium bicarbonate and extracted with ethyl ether and the organic phase is separated after settling has taken place, then dried over magnesium sulphate and evaporated. The residue obtained is purified by chromatography on a silica column and eluted with a mixture of dichloromethane and hexane (50:50). After evaporation of the solvents, 15.2 g (50%) of the expected phenol, melting point 112°–114° C., are collected.

(b) 2-(1-Adamantyl)-5-bromoanisole 1.6 g (53 mmol) of sodium hydride (80% in oil) and 50 ml of THF are introduced into a round-bottomed flask and a solution of 15 g (49 mmol) of the phenol obtained above in (a), dissolved in 100 ml of DMF, is added dropwise. The mixture is stirred until gaseous evolution has ceased and 3.1 ml (49 mmol) of methyl iodide are then introduced. The mixture is stirred at room temperature for four hours, the reaction medium is poured into water and the organic phase is separated after settling has taken place, then dried over magnesium sulphate and evaporated. The residue obtained is ground in the minimum amount of hexane and filtered off. 12.6 g (80%) of 2-(1-adamantyl)-5-bromoanisole, melting point 159°–160° C., are collected.

(c) 4-(1-Adamantyl)-3-methoxybenzoic acid 11.3 g (35 mmol) of the compound obtained above in (b) are dissolved in 50 ml of anhydrous THF. The solution obtained is added dropwise to magnesium (1.3 g; 53 mmol) and a crystal of iodine. After the introduction of the first 5 milliliters, the mixture is heated to reflux and the latter is maintained for two hours after the addition has been completed. The mixture is cooled to −40° C. and a stream of $CO_2$ is passed through it for 30', and the temperature is then allowed to rise to 20° C. The reaction medium is poured into water, the mixture is extracted with ethyl ether and the organic phase is separated after settling has taken place, then dried over magnesium sulphate and evaporated. The residue obtained is purified by chromatography on a silica column and eluted with a mixture of dichloromethane and ethyl ether (90:10). After evaporation of the solvents, 5.1 g (51%) of 4-(1-adamantyl)-3-methoxybenzoic acid, melting point 259°–260° C., are collected.

(d) 4-(1-Adamantyl)-3-methoxybenzoyl chloride

In a manner similar to Example 2(b), starting with 2.9 g (10 mmol) of 4-(1-adamantyl)-3-methoxybenzoic acid, 3.1 g (100%) of crude acid chloride are obtained, which product is used for the next step of the synthesis without further treatment.

(e) Allyl 4-[4-(1-adamantyl)-3-methoxybenzoyloxymethyl]benzoate

In a manner similar to Example 1(d), by reaction of 3.1 g (10 mmol) of the acid chloride obtained above in (d) with 1.92 g (10 mmol) of allyl 4-hydroxymethylbenzoate, 2.9 g (63%) of allyl ester are obtained in the form of a translucent oil.

(f) 4-[4-(1-Adamantyl)-3-methoxybenzoyloxymethyl]benzoic acid

In a manner similar to Example 3(c), starting with 2.7 g (5.8 mmol) of the ester obtained above in (e), 1 g (40%) of 4-[4-(1-adamantyl)-3-methoxybenzoyloxymethyl]benzoic acid, melting point 206°–207° C. is obtained.

Example 11

4-5,6,7,8-Tetrahydro-5,5,8,8-tetramethyl-2-naphthoylthiomethyl)benzoic acid (a) Allyl 4-acetylthiomethylbenzoate 25.7 g (98 mmol) of triphenylphosphine and 100 ml of THF are introduced into a round-bottomed flask and 19.8 g (98 mmol) of diisopropyl azodicarboxylate, dissolved in 150 ml of THF, are added dropwise at 0° C. The mixture is stirred for one hour at 0° C. and a mixture of 9.4 g (49 mmol) of allyl 4-hydroxymethylbenzoate and 7 ml (98 mmol) of thioacetic acid is then added. The mixture is stirred at room temperature for four hours, the reaction medium is poured into water, the mixture is extracted with ethyl ether and the organic phase is separated after settling has taken place, then dried over magnesium sulphate and evaporated. The residue obtained is purified by chromatography on a silica column and eluted with a mixture of dichloromethane and hexane (60:40). 12.2 g (100%) of the expected product are obtained in the form of an oil.

(b) 4-Mercaptomethylbenzoic acid 12.25 g (49 mmol) of ester obtained above in (a) and 100 ml of 2N methanolic sodium hydroxide are introduced into a round-bottomed flask and the mixture is heated to reflux for four hours. The reaction medium is evaporated to dryness, the residue is taken up with water, the mixture is acidified to pH 1 with concentrated hydrochloric acid and extracted with ethyl ether and the organic phase is then dried over magnesium sulphate and evaporated. The residue obtained is ground in the minimum amount of ethyl ether and then filtered off. 6.8 g (83%) of 4-mercaptomethylbenzoic acid, melting point 173°–174° C., are obtained.

(c) 4-(5,6,7,8-Tetrahydro-5,5,8,8-tetramethyl-2-naphthoylthiomethyl)benzoic acid 1.68 g (10 mmol) of 4-mercaptomethylbenzoic acid, 2.8 ml (20 mmol) of triethylamine and 50 ml of THF are introduced into a round-bottomed flask. A solution of 2.5 g (10 mmol) of 5,6,7,8-tetrahydro-5,5,8,8-tetramethyl-2-naphthoyl chloride in 50 ml of THF is added dropwise and the mixture is stirred at room temperature for four hours. The reaction medium is poured into water, the mixture is extracted with ethyl ether and the organic phase is separated after settling has taken place, then dried over magnesium sulphate and evaporated. The residue obtained is ground in 50 ml of a mixture of ethyl ether and hexane (50:50) and then filtered off. 2.5 g (66%) of the expected acid, melting point 150°–151° C., are obtained.

Example 12

4-(5,6,7,8-Tetrahydro-5,5,8,8-tetramethyl-2-naphthylcarboxamidomethyl)benzoic acid (a) Methyl 4-(5,6,7,8-tetrahydro-5,5,8,8-tetramethyl-2-naphthylcarboxamidomethyl)benzoate In a manner similar to Example 1(d), by reaction of 5 g (20 mmol) of 5,6,7,8-tetrahydro-5,5,8,8-tetramethyl-2-naphthoyl chloride with 3.3 g (20 mmol) of methyl 4-aminomethylbenzoate, 7.2 g (95%) of methyl ester, melting point 162°–163° C., are obtained.

(b) 4-(5,6,7,8-Tetrahydro-5,5,8,8-tetramethyl-2-naphthylcarbexamidomethyl)benzoic acid 3.8 g (10 mmol) of the methyl ester obtained above in (a), in 200 ml of 2N methanolic sodium hydroxide, are stirred at room temperature for four hours. The reaction medium is evaporated to dryness, the residue -is taken up with water, the mixture is acidified to pH 1 with concentrated hydrochloric acid and extracted with ethyl ether and the organic phase is separated after settling has taken place, then dried over magnesium sulphate and evaporated. The residue obtained is ground in the minimum amount of ethyl ether and filtered off. 3.2 g (86%) of the expected acid, melting point 275°–276° C., are collected.

Example 13

4(N-Methyl-5,6,7,8-tetrahydro-5,5,8,8-tetramethyl-2-naphthylcarboxamidomethyl)benzoic acid (a) Methyl 4-(N-methyl-5,6,7,8-tetrahydro-5,5,8,8-tetramethyl-2-naphthylcarboxamidomethyl)benzoate 1.6 ml (11 mmol) of diisopropylamine and 50 ml of THF are introduced into a round-bottomed flask. At −78° C., and under a stream of nitrogen, 6.9 ml (11 mmol) of n-butyllithium (1.6M) are added dropwise and the mixture is stirred for 30 minutes. This solution is added dropwise at −78° C., to a solution of 3.8 g (10 mmol) of the methyl ester obtained in 12(a) in 50 ml of THF. The mixture is stirred for 30 minutes. 750 µl (12 mmol) of methyl iodide are added and the temperature is allowed to rise to 20° C. The reaction medium is poured into water, the mixture is extracted with ethyl ether and the organic phase is separated after settling has taken place, then dried over magnesium sulphate and evaporated. The residue obtained is purified by chromatography on a silica column and eluted with a mixture of dichloromethane and ethyl ether (98:2). After evaporation of the solvents, 2.8 g (72%) of methyl ester, melting point 142°–143° C., are obtained.

(b) 4-(N-Methyl-5,6,7,8-tetrahydro-5,5,8,8-tetramethyl-2-naphthylcarbexamidomethyl)benzoic acid In a manner similar to Example 12(b), starting with 1.2 g (30.5 mmol) of the ester obtained above in (a), 1 g (86%) of the expected acid, melting point 181°–182° C., is obtained.

Example 14

4-(5,6,7,8-Tetrahydro-5,5,8,8-tetramethyl-2-naphthylmethyloxycarbonyl)benzoic acid (a) 5,6,7,8-Tetrahydro-5,5,8,8-tetramethyl-2-naphthylmethanol 3.8 g (0.1 tool) of lithium aluminium hydride and 100 ml of THF are introduced into a round-bottomed flask. Under a stream of nitrogen, a solution of 11.6 g (0.05 mol) of 5,6,7,8-tetrahydro-5,5,8,8-tetramethyl-2-naphthoic acid in 100 ml of THF is added dropwise and the mixture is heated to reflux for four hours. The excess hydride is hydrolyzed with 7.2 ml of a 10% solution of sodium potassium tartrate, the precipitate is filtered off and the organic phase is evaporated. 10.6 g (97%) of the expected alcohol, melting point 74°–75° C., are collected.

(b) Diallyl terephthalate

In a manner similar to Example 3(a), starting with 19.4 g (0.1 mol) of dimethyl terephthalate, 18.3 g (75%) of the expected diester are obtained in the form of an oil.

(c) 4-(Allyloxycarbonyl)benzoic acid 12.3 g (50 mmol) of the diester obtained above in (b), 100 ml of THF and 10.5 g (0.25 mol) of lithium hydroxide are introduced into a round-bottomed flask and the mixture is heated to reflux for two hours. The reaction medium is poured into 200 ml of hydrochloric acid (5N) and the solid is filtered off, washed twice with 100 ml of water and dissolved in ethyl ether. The organic phase is dried over magnesium sulphate and evaporated and the residue obtained is purified by chromatography on a silica column and eluted with ethyl ether. 9 g (88%) of 4-(allyloxycarbonyl)benzoic acid, melting point 154°–155° C., are collected.

(d) Allyl 4-(5,6,7,8-tetrahydro-5,5,8,8-tetramethyl-2-naphthylmethyloxycarbonyl)benzoate In a manner similar to Example 4(c), by reaction of 2.06 g (10 mmol) of 4-(allyloxycarbonyl)benzoic acid with 2.18 g (10 mmol) of 5,6,7,8-tetrahydro-5,5,8,8-tetramethyl-2-naphthylmethanol, 2.8 g (70%) of allyl ester are obtained in the form of a translucent oil.

(e) 4-(5,6,7,8-Tetrahydro-5,5,8,8-tetramethyl-2-naphthylmethyloxycarbonyl)benzoic acid In a manner similar to Example 3(c), starting with 2.6 g (6.4 mmol) of the ester obtained above in (d), 1.7 g (74%) of 4-(5,6,7,8-tetrahydro-5,5,8,8-tetramethyl-2-naphthylmethyloxycarbonyl)benzoic acid, melting point 171°–172° C., are obtained.

Example 15

4-[(5,6,7,8-Tetrahydro-5,5,8,8-tetramethyl-2-naphthylmethylthio)carbonyl]benzoic acid (a) 5,6,7,8-Tetrahydro-5,5,8,8-tetramethyl-2-naphthylmethyl S-thioacetate In a manner similar to Example 11(a), starting with 4.36 g (20 mmol) of 5,6,7,8-tetrahydro-5,5,8,8-tetramethyl-2-naphthylmethanol, 5.1 g (93%) of the expected product are obtained.

(b) 5,6,7,8-Tetrahydro-5,5,8,8-tetramethyl-2-naphthylmethanethiol

In a manner similar to Example 11(b), starting with 4.8 g (17.4 mmol) of the product obtained above in (a), 3.7 g (93%) of the expected thiol are obtained in the form of a slightly yellow oil.

(c) Allyl 4-[(5,6,7,8-tetrahydro5,5,8,8tetramethyl-2-naphthyimethylthio)carbonyl]benzoate In a manner similar to Example 4(c), by reaction of 2 g (10 mmol) of 4-(allyloxycarbonyl)benzoic acid with 2.34 g (10 mmol) of 5,6,7,8-tetrahydro-5,5,8,8-tetramethyl-2-naphthylmethanethiol, 3.4 g (81%) of the expected allyl ester, melting point 79°–80° C., are obtained.

(d) 4-[(5,6,7,8-Tetrahydro-5,5,8,8-tetramethyl-2-naphthylmethylthio)carbonyl]benzoic acid In a manner similar to Example 3(c), starting with 3.3 g (7.8 mmol) of the ester obtained above in (c), 2.7 g (90%) of 4-[(5,6,7,8-tetrahydro-5,5,8,8-tetramethyl-2-naphthylmethylthio)carbonyl]benzoic acid, melting point 162°–163° C., are obtained.

Example 16

5-(5,6,7,8-Tetrahydro-5,5,8,8-tetramethyl-2-naphthoyloxymethyl)-2-thiophenecarboxylic acid (a) Allyl 5-formyl-2-thiophenecarboxylate In a manner similar to Example 7(a), starting with 5.5 g (35 mmol) of 5-formyl-2-thiophenecarboxylic acid, 5 g (73%) of allyl ester are obtained.

(b) Allyl 5-hydroxymethyl-2-thiophenecarboxylate

In a manner similar to Example 7(b), starting with 5 g (25.5 mmol) of allyl 5-formyl-2-thiophenecarboxylate, 5 g (100%) of the expected product are obtained in the form of a colorless oil.

(c) Allyl 5-(5,6,7,8-tetrahydro-5,5,8,8-tetramethyl-2-naphthoyloxymethyl)-2-thiophenecarboxylate In a manner similar to Example 1(d), by reaction of 2.5 g (10 mmol) of 5,6,7,8-tetrahydro-5,5,8,8-tetramethyl-2-naphthoyl chloride with 1.98 g (10 mmol) of allyl 5-hydroxymethyl-2-thiophene carboxylate, 3.7 g (90%) of allyl ester are obtained in the form of a colorless oil.

(d) 5-(5,6,7,8-Tetrahydro-5,5,8,8-tetramethyl-2-naphthoyloxymethyl)-2-thiophenecarboxylic acid In a manner similar to Example 3(c), starting with 3.4 g (8.4 mmol) of the ester obtained above in (c), 2.7 g (87%) of 5-(5,6,7,8-tetrahydro-5,5,8,8-tetramethyl-2-naphthoyloxymethyl)-2-thiophenecarboxylic acid, melting point 155°–156° C., are obtained.

Example 17

4-(5,6,7,8-Tetrahydro-5,5,8,8-tetramethyl-2-naphthyloxycarboxamido)benzoic acid

(a) 5,6,7,8-Tetrahydro-5,5,8,8-tetramethyl-2-naphthyl chloroformate 4.1 g (20 mmol) of 5,6,7,8-tetrahydro-5,5,8,8-tetramethyl-2-naphthol, 1.2 ml of trichloromethyl chloroformate and 40 ml of benzene are introduced into a round-bottomed flask. 3 ml (21 mmol) of triethylamine are added dropwise and the mixture is stirred at room temperature for twelve hours. The reaction medium is poured into water, the mixture is extracted with ethyl ether and the organic phase is separated after settling has taken place, then dried over magnesium sulphate and evaporated. The residue obtained is purified by chromatography on a silica column and eluted with a mixture of dichloromethane and hexane (40:60). After evaporation of the solvents, 4 g (75%) of the expected chloroformate are collected in the form of a colorless oil.

(b) Benzyl 4-(5,6,7,8-tetrahydro 5,5,8,8-tetramethyl-2-naphthyloxycarboxamido)benzoate 835 mg (3.7 mmol) of benzyl 4-aminobenzoate, 300 µl (3.7 mmol) of pyridine and 20 ml of dichloromethane are introduced into a round-bottomed flask. A solution of 980 mg (3.7 mmol) of the chloroformate obtained above in (a), dissolved in 20 ml of dichloromethane, is added dropwise and the mixture is stirred at room temperature for twelve hours. The reaction medium is poured into water, the mixture is extracted with ethyl ether and the organic phase is separated after settling has taken place, then dried over magnesium sulphate and evaporated. The residue obtained is ground in the minimum amount of hexane and filtered off. 1.6 g (95%) of benzyl ester are collected.

(c) 4-(5,6,7,8-Tetrahydro-5,5,8,8-tetramethyl-2-naphthyloxycarboxamido)benzoic acid In a manner similar to Example 2(d), starting with 1.5 g (3.3 mmol) of the ester obtained above in (b), 1 g (83%) of the expected acid, melting point 213°–214° C., is obtained.

Example 18

4-[5,6,7,8-Tetrahydro-5,5,8,8-tetramethyl-2-naphthyl (carbonyldioxy)]benzoic acid

(a) Benzyl 4-[5,6,7,8-tetrahydro-5,5,8,8-tetramethyl-2-naphthyl(carbonyldioxy)]benzoate In a manner similar to Example 17(b), by reaction of 3.9 g (14.6 mmol) of the chloroformate prepared in 17(a) with 3.33 g (14.6 mmol) of benzyl 4-hydroxybenzoate, 5.3 g (79%) of benzyl ester are obtained in the form of an oil.

(b) 4-[5,6,7,8-Tetrahydro-5,5,8,8-tetramethyl-2-naphthyl(carbonyldioxy)]benzoic acid In a manner similar to Example 2(d), starting with 2.9 g (6 mmol) of the benzyl ester obtained above in (a), 1.7 g (77%) of the expected acid, melting point 81°–182° C., are obtained.

Example 19

4-[3-(1-Adamantyl)-4-methoxyphenoxycarboxamido]benzoic acid

(a) 3-(1-Adamantyl)-4-methoxyphenol 4.2 g (0.17 mol) of magnesium, a crystal of iodine and 50 ml of THF are introduced into a three-necked flask. A solution of 50 g (0.156 mol) of 2-(1-adamantyl)-4-bromoanisole in 200 ml of THF is added dropwise and the mixture is heated to reflux for three hours.

This solution is added dropwise at 0° C., to a solution of 19.2 ml (0.172 mol) of trimethyl borate in 400 ml of ethyl ether, the mixture is then stirred at room temperature for one hour, 200 ml of water are added and the reaction medium is evaporated to dryness. The residue is cooled to 10° C. and a solution of 40 g of ammonium chloride dissolved in 150 ml of water and then 100 ml of hydrogen peroxide (30%) are added successively, and the mixture is stirred at room temperature for six hours. The solid is filtered off, washed with water, dried over phosphorus pentoxide, ground in 400 ml of hexane heated to reflux and filtered off. 22.9 g (57%) of the expected phenol, melting point 167°–169° C., are collected.

(b) 3-(1-Adamantyl)-4-methoxyphenyl chloroformate

In a manner similar to Example 17(a), starting with 6.45 g (25 mmol) of 3-(1-adamantyl)-4-methoxyphenol, 5 g (62%) of the expected chloroformate, melting point 87°–89° C., are obtained.

(c) Benzyl 4-[3-(1-adamantyl)-4-methoxyphenoxycarboxamido]benzoate

In a manner similar to Example 17(b), by reaction of 2.4 g (7.5 mmol) of chloroformate obtained above in (b) with 1.7 g (7.5 mmol) of benzyl 4-aminobenzoate, 3.2 g (84%) of the expected benzyl ester, melting point 208°–209° C., are obtained.

(d) 4-[3-(1-Adamantyl)-4-methoxyphenoxycarboxamido]benzoic acid

In a manner similar to Example 2(d), starting with 2 g (3.9 mmol) of the benzyl ester obtained above in (c), 1.2 g (73%) of the expected acid, melting point 69°–271° C., are obtained.

Example 20

4-[3-(1-Adamantyl)-4-methoxyphenyl (carbonyldioxy]benzoic acid

(a) Benzyl 4-[3-(1-adamantyl)-4-methoxyphenyl (carbonyldioxy)]benzoate

In a manner similar to Example 17(b), by reaction of 2.5 g (7.8 mmol) of chloroformate obtained in 19(b) with 1.8 g (7.8 mmol) of benzyl 4-hydroxybenzoate, 3.1 g (77%) of the expected benzyl ester, melting point 116°–118° C., are obtained.

(b) 4-[3-(1-Adamantyl)-4-methoxyphenyl(carbonyldioxy)]benzoic acid

In a manner similar to Example 2(d), starting with 2 g (3.9 mmol) of the benzyl ester obtained above in (a), 1.35 g (83%) of the expected acid, melting point 238°–239° C., are obtained.

Example 21

4-[1-(5,6,7,8-Tetrahydro-5,5,8,8-tetramethyl-2-naphthoyloxy)ethyl]benzoic acid

(a) Allyl 4-acetylbenzoate 1.65 g (55 mmol) of sodium hydride (80% in oil) and 50 ml of DMF are introduced under a stream of nitrogen into a round-bottomed flask. 8.2 g (50 mmol) of 4-acetylbenzoic acid, dissolved in 100 ml of DMF, are added dropwise and the mixture is stirred at room temperature until gaseous evolution has ceased. 4.6 ml (55 mmol) of allyl bromide are then introduced and the mixture is stirred at room temperature for 24 hours. The reaction medium is poured into water, the mixture is extracted with ethyl ether and the organic phase is separated after settling has taken place, then dried over magnesium sulphate and evaporated. The residue obtained is purified by chromatography on a silica column, eluting with a mixture of dichloromethane and hexane (80:20). After evaporation of the solvents, 7.2 g (71%) of allyl ester are collected in the form of a colorless oil.

(b) Allyl 4-(1-hydroxyethyl)benzoate 3.1 g (15 mmol) of the allyl ester obtained above in (a), 20 ml of methyl alcohol and 20 ml of THF are introduced into a round-bottomed flask. While cooling in an icebath, 285 mg (7.5 mmol) of sodium borohydride are added in small portions and the mixture is stirred at room temperature for one hour. The reaction medium is poured into water, the mixture is extracted with ethyl ether and the organic phase is separated after settling has taken place, then dried over magnesium sulphate and evaporated. 3.1 g (100%) of the expected product are collected in the form of a colorless oil.

(c) Allyl 4-[1-(5,6,7,8-tetrahydro-5,5,8,8-tetramethyl-2-naphthoyloxy)ethyl]benzoate In a manner similar to Example 4(c), by reaction of 3 g (12.9 mmol) of 5,6,7,8-tetrahydro-5,5,8,8-tetramethyl-2-naphthoic acid with 2.65 g (12.9 mmol) of allyl 4-(1-hydroxyethyl)benzoate, 2.8 g (52%) of the expected allyl ester are obtained in the form of a slightly yellow oil.

(d) 4-[1-(5,6,7,8-Tetrahydro-5,5,8,8-tetramethyl-2-naphthoyloxy)ethyl]benzoic acid In a manner similar to Example 3(c), starting with 2.8 g (6.7 mmol) of the allyl ester obtained above in (c), 2 g (79%) of the expected acid, melting point 149°–150° C., are obtained.

Example 22

4-{[1-(5,6,7,8-Tetrahydro-5,5,8,8-tetramethyl-2-naphthyl)ethyloxy]carbonyl}benzoic acid

(a) Allyl 4-{[1-(5,6,7,8-tetrahydro-5,5,8,8-tetramethyl-2-naphthyl)ethyloxy]carbonyl}benzoate In a manner similar to Example 4(c), by reaction of 2.1 g (10 mmol) of 4-(allyloxycarbonyl)benzoic acid with 2.3 g (10 mmol) of 1-(5,6,7,8-tetrahydro-5,5,8,8-tetramethyl-2-naphthyl)ethanol, 3.2 g (76%) of the expected allyl ester are obtained in the form of a colorless oil.

(b) 4-{[1-(5,6,7,8-Tetrahydro-5,5,8,8-tetramethyl-2-naphthyl)ethyloxy]carbonyl}benzoic acid In a manner similar to Example 3(c), starting with 2.8 g (6.6 mmol) of the allyl ester obtained above in (a), 2.3 g (92%) of the expected acid, melting point 176°–177° C., are obtained.

Example 23

4-[3-(1-Adamantyl)-4-methoxyphenylacetamido]benzoic acid

(a) Methyl 3-(1-adamantyl)-4-hydroxyphenylacetate

In a manner similar to Example 10(a), by reaction of 4.6 g (38 mmol) of 1-adamantanol with 5 g (30 mmol) of methyl 4-hydroxyphenylacetate, 4.9 g (54%) of methyl 3-(1-adamantyl)-4-hydroxyphenylacetate, melting point 185°–186° C., are obtained.

(b) Methyl 3-(1-adamantyl)-4-methoxyphenylacetate

In a manner similar to Example 10(b), by reaction of 3 g (18 mmol) of ester obtained above in (a) with 750 μl (12 mmol) of methyl iodide, 1.3 g (40%) of the expected ester, melting point 70°–71° C., are obtained.

(c) 3-(1-Adamantyl)-4-methoxyphenylacetic acid

In a manner similar to Example 12(b), starting with 1.27 g (4 mmol) of the ester obtained above in (b), 1.12 g (93%) of 3-(1-adamantyl)-4-methoxyphenylacetic acid, melting point 223°–224° C., are obtained.

(d) 3-(1-Adamantyl)-4-methoxyphenylacetyl chloride

In a manner similar to Example 2(b), starting with 1.1 g (3.7 mmol) of the acid obtained above in (c) and after washing in hexane, 860 mg (74%) of the acid chloride, melting point 78°–79° C., are obtained.

(e) Methyl 4-[3-(1-adamantyl)-4-methoxyphenylacetamido]benzoate

In a manner similar to Example 1(d), by reaction of 3.8 g (11.9 mmol) of 3-(1-adamantyl)-4-methoxyphenylacetyl chloride with 1.81 g (12 mmol) of methyl 4-aminobenzoate, 3.2 g (63%) of the expected methyl ester, melting point 146°–147° C., are obtained.

(f) 4-[3-(1-Adamantyl)-4-methoxyphenylacetamido]benzoic acid

In a manner similar to Example 12(b), starting with 3 g (6.9 mmol) of the ester obtained above in (e), 2.2 g (76%) of the expected acid, melting point 238°–240° C., are obtained.

Example 24

4-(5,6,7,8-Tetrahydro-5,5,8,8-tetramethyl-2-naphthoylformamido)benzoic acid

(a) Allyl 4-(5,6,7,8-tetrahydro-5,5,8,8-tetramethyl-2-naphthoylformamido)benzoate In a manner similar to Example 1(d), by reaction of 5.6 g (20 mmol) of 5,6,7,8-tetramethyl-2-naphthylglyoxyloyl chloride with 3.6 g (20 mmol) of allyl 4-aminobenzoate, 3.5 g (42%) of the expected ester are obtained in the form of a slightly yellow oil.

(b) 4-(5,6,7,8-tetrahydro-5,5,8,8-tetramethyl-2-naphthoylformamido)benzoic acid 105 mg (3.5 mmol) of sodium hydride (80% in oil) and 5 ml of THF are introduced under a stream of nitrogen into a round-bottomed flask. 530 μl (3.5 mmol) of diethyl malonate are then added dropwise and the mixture is stirred until gaseous evolution has ceased. This solution is introduced dropwise into a mixture of 1.47 g (3.5 mmol) of the allyl ester prepared in Example 24(a) and 210 mg (0.18 mmol) of tetrakis(triphenylphosphine)palladium(O) and the mixture is stirred at room temperature for one hour. The reaction medium is poured into water, the mixture is extracted with ethyl ether and the organic phase is separated after settling has taken place, dried over magnesium sulphate and evaporated. The residue obtained is purified by chromatography on a silica column and eluted with a mixture of dichloromethane and ethyl ether (95:5). After evaporation of the solvents, 1.1 g (85%) of acid, melting point 216°–217° C., are collected.

Example 25

4-(α-Hydroxy-5,6,7,8-tetrahydro-5,5,8,8-tetramethyl-2-naphthylacetamido)benzoic acid (a) Allyl 4-(α-hydroxy-5,6,7,8-tetrahydro-5,5,8,8-tetramethyl-2-naphthylacetamido)benzoate In a manner similar to Example 5(b), starting with 1.47 g (3.5 mmol) of the ester prepared in Example 24(a), 1.3 g (90%) of the expected ester are obtained in the form of a colorless oil.

(b) 4-(α-Hydroxy-5,6,7,8-tetrahydro-5,5,8,8-tetramethyl-2-naphthylacetamido)benzoic acid In a manner similar to Example 24(b), starting with 1.3 g (3.1 mmol) of the ester prepared in Example 25(a), 1.1 g (93%) of 4-(α-hydroxy-5,6,7,8-tetrahydro-5,5,8,8-tetramethyl-2-naphthylacetamido)benzoic acid, melting point 220°–221° C., are obtained.

Example 26

4-(5,6,7,8-Tetrahydro-5,5,8,8-tetramethyl-2-naphthylcarbamoylmethyl)benzoic acid (a) 4-(tert-Butyoxycarbonylmethyl)benzoic acid 11.4 g (0.170 mol) of powdered zinc and 50 ml of THF are introduced into a three-necked flask, 2.2 ml of trimethylsilyl chloride are added and the mixture is stirred for 15 minutes, 28 ml (0.174 mol) of tert-butyl 2-bromoacetate are then introduced dropwise and the mixture is stirred for 30 minutes. It is cooled to 0° C., (icebath), 5 g (4.3 mmol) of tetrakis(triphenylphosphine)palladium(O), 10.8 g (43.5 mmol) of 4-iodobenzoic acid and 50 ml of HMPA are introduced and the mixture is heated to 40° C., for one hour. The reaction medium is poured into water, the mixture is extracted with ethyl ether and the organic phase is separated after settling has taken place, dried over magnesium sulphate and evaporated. The residue obtained is purified by chromatography on a silica column and eluted with a mixture of dichloromethane and ethyl ether (95:5). After evaporation of the solvents, 8.1 g (80%) of the expected product, melting point 132°–133° C., are collected.

(b) tert-Butyl 4-(allyloxycarbonyl)phenylacetate

In a manner similar to Example 7(a), starting with 7.9 g (33.4 mmol) of 4-(tert-butoxycarbonylmethyl)benzoic acid, 8 g (87%) of the allyl ester are obtained in the form of a colorless oil.

(c) 4-(Allyloxycarbonyl)phenylacetic acid

In a manner similar to Example 1(e), starting with 7.4 g (26.8 mmol) of the diester obtained above in (b), 5.8 g (100%) of the expected monoacid, melting point 68°–69° C., are obtained.

(d) Allyl 4-(5,6,7,8-tetrahydro-5,5,8,8-tetramethyl-2-naphthylcarbamoylmethyl)benzoate In a manner similar to Example 4(c), by reaction of 2 g (10 mmol) of 5,6,7,8-tetrahydro-5,5,8,8-tetramethyl-2-naphthylamine with 2.2 g (10 mmol) of 4-(allyloxycarbonyl)phenylacetic acid, 3.7 g (92%) of the expected ester, melting point 49°–50° C., are obtained.

(e) 4-(5,6,7,8-Tetrahydro-5,5,8,8-tetramethyl-2-naphthylcarbamoylmethyl)benzoic acid In a manner similar to Example 24(b), starting with 3.5 g (8.6 mmol) of the ester obtained above in (d), 1.4 g (47%) of the expected acid, melting point 249°–250° C., are obtained.

Example 27

2-Hydroxy-4-(5,6,7,8-tetrahydro-5,5,8,8-tetramethyl-2-naphthylacetoxy)benzoic acid (a) Benzyl 2-hydroxy-4-(5,6,7,8-tetrahydro-5,5,8,8-tetramethyl-2-naphthylacetoxy)benzoate In a manner similar to Example 1(d), by reaction of 2.44 g (10 mmol) of benzyl 2,4-dihydroxybenzoate with 2.6 g (10 mmol) of 5,6,7,8-tetrahydro-5,5,8,8-tetramethyl-2-naphthylacetyl chloride, 3.9 g (83%) of the expected ester are obtained in the form of a colorless oil.

(b) 2-Hydroxy-4-(5,6,7,8-tetrahydro-5,5,8,8-tetramethyl-2-naphthylacetoxy)benzoic acid In a manner similar to Example 2(d), starting with 3.4 g (7.2 mmol) of the ester obtained above in (a), 2.5 g (91%) of acid, melting point 163°–164° C., are obtained.

Example 28

4-(5,6,7,8-Tetrahydro-5,5,8,8-tetramethyl-2-naphthyloxycarbonylmethyl)benzoic acid (a) tert-Butyl 4-(benzyloxycarbonyl)phenylacetate In a manner similar to Example 7(a), by reaction of 3 g (12.7 mmol) of 4-(tert-butoxycarbonylmethyl)benzoic acid prepared in Example 29(a) with 1.6 ml (14 mmol) of benzyl bromide, 3.2 g (77%) of the benzyl ester are obtained in the form of a slightly yellow oil.

(b) 4-(Benzyloxycarbonyl)phenylacetic acid

In a manner similar to Example 1(e), starting with 3.1 g (9.5 mmol) of the above diester, 2.3 g (90%) of the expected monoester, melting point 107°–108° C., are obtained.

(c) Benzyl 4-(5,6,7,8-tetrahydro-5,5,8,8-tetramethyl-2-naphthyloxycarbonylmethyl)benzoate In a manner similar to Example 4(c), by reaction of 1.97 g (7.3 mmol) with 1.48 g (7.3 mmol) of 5,6,7,8-tetrahydro- 5,5,8,8-tetramethyl-2-naphthol, 2.5 g (75%) of the expected product are obtained in the form of a colorless oil.

(d) 4-(5,6,7,8-Tetrahydro-5,5,8,8-tetramethyl-2-naphthyloxycarbonylmethyl)benzoic acid In a manner similar to Example 2(d), starting with 2.43 g (5.2 mmol) of the above benzyl ester, 1.1 g (58%) of acid, melting point 131°–132° C., are obtained.

Example 29

4-(N-Methyl-5,6,7,8-tetrahydro-5,5,8,8-tetramethyl-2-naphthylacetamido)benzoic acid

(a) Methyl 4-(N-methyl-5,6,7,8-tetrahydro-5,5,8,8-tetramethyl-2-naphthylacetamido)benzoate In a manner similar to Example 4(c), by reaction of 2.46 g (10 mmol) of 5,6,7,8-tetrahydro-5,5,8,8-tetramethyl-2-naphthylacetic acid with 1.65 g (10 mmol) of methyl 4-methylaminobenzoate, 2.1 g (54%) of the expected product are obtained in the form of a colorless oil.

(b) 4-(N-Methyl-5,6,7,8-tetrahydro-5,5,8,8-tetramethyl-2-naphthylacetamido)benzoic acid 1.8 g (4.6 mmol) of the ester obtained above in (a), 100 ml of 2N methanolic sodium hydroxide and 50 ml of TMF are introduced into a round-bottomed flask. The mixture is stirred at room temperature for one hour and evaporated to dryness, the residue is taken up with water, the mixture is extracted with ethyl ether and the aqueous phase is separated after settling has taken place. The aqueous phase is acidified to pH 1 with concentrated hydrochloric acid and extracted with ethyl ether and the organic phase is separated after settling has taken place, dried over magnesium sulphate and evaporated. 1.6 g (94%) of the expected acid, having a melting point of 192°–193° C., are collected.

Example 30

4-(α-Fluoro-5,6,7,8-tetrahydro-5,5,8,8-tetramethyl-2-naphthylacetamido)benzoic acid

(a) Ethyl α-hydroxy-5,6,7,8-tetrahydro-5,5,8,8-tetramethyl-2-naphthylacetate In a manner similar to Example 5(b), starting with 10.3 g (35.7 mmol) of ethyl 5,6,7,8-tetrahydro-5,5,8,8-tetramethyl-2-naphthylglyoxylate, 7.5 g (73%) of the expected alcohol are obtained in the form of a slightly yellow oil.

(b) Ethyl α-fluoro-5,6,7,8-tetrahydro-5,5,8,8-tetramethyl-2-naphthylacetate 2.9 g (10 mmol) of the above alcohol and 50 ml of dichloromethane are introduced into a round-bottomed flask. Under a stream of nitrogen and at −78° C., a solution of 1.3 ml of diethylaminosulphur trifluoride (DAST) in 30 ml of dichloromethane is added dropwise and the temperature is allowed to rise to 25° C. The reaction medium is poured into water, the mixture is extracted with ethyl ether and the organic phase is separated after settling has taken place, dried over magnesium sulphate and evaporated. The residue is purified by chromatography on a silica column and eluted with a mixture of dichloromethane and hexane (20:80). After evaporation of the solvents, 2.3 g (79%) of the expected fluoro compound is collected in the form of a colorless oil.

(c) α-Fluoro-5,6,7,8-tetrahydro-5,5,8,8-tetramethyl-2-naphthylacetic acid 2.3 g (7.8 mmol). of the above fluoro ester, 100 ml of hydrochloric acid (10%) and 50 ml of THF are introduced into a round-bottomed flask. The mixture is heated to reflux for 24 hours and evaporated to dryness, the residue is taken up with ether and the organic phase is washed with water, dried over magnesium sulphate and evaporated. The residue obtained is ground in hexane and, after filtration, 1.5 g (75%) of acid, melting point 127°–128° C., are collected.

(d) Allyl 4-(α-fluoro-5,6,7,8-tetrahydro-5,5,8,8-tetramethyl-2-naphthylacetamido)benzoate In a manner similar to Example 4(c), by reaction of 1.35 g (5.1 mmol) of α-fluoro-5,6,7,8-tetrahydro-5,5,8,8-tetramethyl-2-naphthylacetic acid with 920 mg (5.1 mmol) of allyl 4-aminobenzoate, 1.7 g (81%) of ester are obtained in the form of an oil.

(e) 4-(α-Fluoro-5,6,7,8-tetrahydro-5,5,8,8-tetramethyl-2-naphthylacetamido)benzoic acid In a manner similar to Example 3(c), starting with 1.56 g (3.7 mmol) of the above ester, 1.3 g (93%) of 4-(α-fluoro-5,6,7,8-tetrahydro-5,5,8,8-tetramethyl-2-naphthylcetamido)benzoic acid, melting point 213°–214° C., are collected.

Example 31

4-[3-(1-Adamantyl)-4-methoxyphenylureido]benzoic acid

(a) 3-(1-Adamantyl)-4-methoxy-N-(trifluoroacetyl)aniline 11.70 ml (84 mmol) of triethylamine in 10 ml of tetrahydrofuran and 8.70 ml (91 mmol) of ethyl chloroformate in 10 ml of tetrahydrofuran are successively added dropwise to a solution of 20.6 g (70 mmol) of 3-(1-adamantyl)-4-methoxybenzoic acid in 200 ml of tetrahydrofuran at 0° C. The reaction medium is stirred for 40 minutes at 0° C., 6.83 g (105 mmol) of sodium azide, dissolved in 30 ml of water, are then added to this medium and the mixture is left stirring at 0° C. for 2 hours. The reaction medium is poured into ice-cold water, the mixture is extracted with dichloromethane and the organic phase is washed with water, dried over magnesium sulphate and evaporated. The residue is dissolved in 400 ml of dichloromethane, 7.3 ml (0.094 mol) of trifluoroacetic acid are added and the mixture is heated to reflux for 30 hours. The reaction medium is poured into saturated sodium bicarbonate solution and the organic phase is dried over magnesium sulphate and evaporated. The residue is chromatographed on silica with a dichloromethane/hexane (30:70) mixture to yield 14.1 g (57%) of 3-(1-adamantyl)-4-methoxy-N-(trifluoroacetyl)aniline, melting point 166°–167° C.

(b) 3-(1-Adamantyl)-4-methoxyaniline 11.03 g (31.2 mmol) of 3-(1-adamantyl)4-methoxy-N-(trifluoroacetyl)aniline dissolved in 40 ml of methanol and 160 ml of water are treated with 7.12 g (51.5 mmol) of potassium hydroxide. The reaction medium is heated to 50° C. for 20 hours and then 80° C. for 18 hours. After evaporation to dryness, the residue is taken up with ethyl ether, the insoluble matter is filtered off and the filtrate is dried over magnesium sulphate and evaporated. The solid is washed in hexane to yield, after drying, 7.44 g (93%) of 3-(1-adamantyl)-4-methoxyaniline, melting point 140°–141° C.

27

(c) Methyl 4-[3-(1-adamantyl)-4-methoxyphenylureido]benzoate

A solution of 2.81 g (15.6 mmol) of 4-(methoxycarbonyl) benzoic acid in 30 ml of tetrahydrofuran is placed at 0° C., then treated with 2.61 ml (18.7 mmol) of triethylamine and 1.94 ml (20.3 mmol) of ethyl chloroformate and left stirring for 1 hour at 0° C. A solution of 1.52 g (23.4 mmol) of sodium azide in 10 ml of water is added to this medium, the mixture is left stirring at 0° C. for 3 hours and the reaction medium is then poured into ice-cold water and extracted with ethyl ether. The organic phase is washed with water, dried over magnesium sulphate and evaporated. The residue is dissolved in 30 ml of toluene, heated to 100° C. for 1.5 hours and then cooled to room temperature. 4.82 g (18.7 mmol) of 3-(1-adamantyl)-4-methoxyaniline are then added dropwise to the foregoing solution and the mixture is stirred at 50° C. for 1.5 hours. It is evaporated to dryness, the solid is taken up with ethyl ether and the organic phase is dried over magnesium sulphate and evaporated. The residue is recrystallized in ethyl acetate to yield 6.16 g (91%) of methyl 4-[3-(1-adamantyl)-4-methoxyphenylureido] benzoate, melting point 223°–224° C.

(d) 4-[3-(1-Adamantyl)-4-methoxyphenylureido] benzoic acid 6 g (0.15 mol) of sodium hydroxide are added to a solution of 6.08 g (14 mmol) of methyl 4-[3-(1-adamantyl) -4-methoxyphenylureido]benzoate in 75 ml of methanol and the mixture is stirred at room temperature for 3 hours and then heated to reflux for 3.5 hours. The reaction mixture is evaporated, the residue is then taken up with 100 ml of water and the mixture is acidified to pH 1. The solid is filtered off, rinsed with water, dried and recrystallised in a tetrahydrofuran/hexane mixture to yield 2.78 g (87%) of 4-[3-(1-adamantyl)-4-methoxyphenylureido]benzoic acid, melting point 279°–282° C.

Example 32

2-Hydroxy-4-(5,6,7,8-tetrahydro-5,5,8,8-tetramethyl-2-naphthoylmethyloxy)benzoic acid

(a) Allyl 2-hydroxy-4-(5,6,7,8-tetrahydro-5,5,8,8-tetramethyl-2-naphthoylmethyloxy)benzoate 0.01 mol of sodium hydride (80% in oil) and 20 ml of DMF are introduced into a round-bottomed flask. A solution of 1.9 g (0.01 mol) of allyl 2,4-dihydroxybenzoate dissolved in 50 ml of DMF is added dropwise and the mixture is stirred until gaseous evolution has ceased. A solution of 3.1 g (0.01 mol) of 2-(2'-bromoaceto)-5,6,7,8-tetrahydro-5,5,8,8-tetramethylnaphthone in 20 ml of DMF is then introduced.

After stirring for 4 hours at room temperature, extraction and chromatography on a silica column, 3.4 g (81%) of allyl ester are obtained in the form of a slightly yellow oil.

(b) 2-Hydroxy-4-(5,6,7,8-tetrahydro-5,5,8,8-tetramethyl-2-naphthoylmethyloxy)benzoic acid In a manner similar to Example 3(c), starting with 3.4 g (8 mmol) of the above allyl ester, 640 mg (21%) of the expected acid, melting point 202°–3° C., are obtained.

Example 33

4-(α-Methylene-5,6,7,8-tetrahydro-5,5,8,8-tetramethyl-2-naphthylacetamido)benzoic acid

(a) Methyl 4-(α-methylene-5,6,7,8-tetrahydro-5,5,8,8-tetramethyl-2-naphthylacetamido)benzoate In a manner similar to Example 4(c), by reaction of 4.6 g (18 mmol) of α-methylene-5,6,7,8-tetrahydro-5,5,8,8-tetramethyl-2-naphthylacetic acid with 2.7 g (18 mmol) of methyl 4-aminobenzoate, 2.4 g (34%) of the expected ester are obtained in the form of a colorless oil.

(b) 4-(α-Methylene-5,6,7,8-tetrahydro-5,5,8,8-tetramethyl-2-naphthylacetamido)benzoic acid In a manner similar to Example 12(b), starting with 2.2 g (5.6 mmol) of the above methyl ester, 1.6 g (76%) of the expected acid, melting point 207°–8° C., are obtained.

Example 34

4-[2-(5,6,7,8-Tetrahydro-5,5,8,8-tetramethyl-2-naphthyl)propionamido]benzoic acid 650 mg (1.7 mmol) of 4-(α-methylene-5,6,7,8-tetrahydro-5,5,8,8-tetramethyl-2-naphthylacetamido) benzoic acid, 100 mg of palladium on charcoal (10%) and 100 ml of dioxane are introduced into a reactor. The mixture is hydrogenated at room temperature and under a pressure of 7 bars for 2 h, the catalyst is filtered off and the filtrate is evaporated. The residue obtained is ground in the minimum amount of ethyl ether, filtered off and dried 580 mg (89%) of acid, melting point 195°–6° C., is obtained.

Example 35

Methyl 2-hydroxy-4-(5,6,7,8-tetrahydro-5,5,8,8-tetramethyl-2-naphthoylformamido)benzoate 6.7 g (40 mmol) of methyl 2-hydroxy-4-aminobenzoate, 10 ml (0.12 mol) of pyridine and 50 ml of THF are introduced into a round-bottomed flask. A solution of 10.5 g (40 mmol) of 5,6,7,8-tetrahydro-5,5,8,8-tetramethyl-2-naphthylglyoxyloyl chloride, prepared in 1(c), in 100 ml of THF is added dropwise and the mixture is stirred at room temperature for 4 h. The reaction medium is poured into water, the mixture is extracted with ethyl ether and the organic phase is separated after settling has taken place, dried over magnesium sulphate and evaporated. The residue obtained is purified by chromatography on a silica column and eluted with a mixture of dichloromethane and hexane (30:70). After evaporation of the solvents, 7.3 g (45%) of methyl ester, melting point 146°–7° C., are collected.

Example 36

2-Hydroxy-4-(α-hydroxy-5,6,7,8-tetrahydro-5,5,8,8-tetramethyl-2-naphthylacetamido)benzoic acid

(a) Methyl 2-hydroxy-4-(α-hydroxy-5,6,7,8-tetrahydro-5,5,8,8-tetramethyl-2-naphthylacetamido) benzoate 2.8 g (7 mmol) of the methyl ester obtained in Example 35, 50 ml of THF and 50 ml of methyl alcohol are introduced under a stream of nitrogen into a round-bottomed flask. While cooling in an icebath, 130 mg (3.5 mol) of sodium borohydride are added in small portions and the mixture is stirred at room temperature for 2 h.

The reaction medium is poured into water, the mixture is extracted with ethyl ether and the organic phase is separated after settling has taken place, dried over magnesium sulphate and evaporated. 2.8 g (100%) of methyl ester, melting point 168°–9° C., are collected.

(b) 2-Hydroxy-4-(α-hydroxy-5,6,7,8-tetrahydro-5,5,8,8-tetramethyl-2-naphthylacetamido)benzoic acid In a manner similar to Example 12(b), starting with 2.8 g (6.8 mmol) of the above methyl ester, 2 g of the expected acid, melting point 178°–9° C., are obtained.

Example 37

2-Hydroxy-4-(3,5-di-tert-butyl-4-hydroxybenzoylmethyloxy)benzoic acid

(a) 2'-Bromo-3,5-di-tert-butyl-4-hydroxyacetophenone 2.5 g (0.01 mol) of 3,5-di-tert-butyl-4-hydroxyacetophenone, 25 ml of ethyl ether and 25 ml of dioxane are introduced into a round bottomed flask. 0.01 mol of bromine is added dropwise and the mixture is stirred at room temperature for 1 hour. After extraction and evaporation of the solvents, the residue is chromatographed on a silica column. After evaporation of the elution solvent, 1.5 g (46%) of the bromo derivative, melting point 103°–4° C., are obtained.

(b) Benzyl 2-hydroxy-4-(3,5-di-tert-butyl-4-hydroxybenzoylmethyloxy)benzoate

In a manner similar to Example 32(a), by reaction of 1.5 g (4.6 mmol) of the above bromo derivative with 1.2 g (4.9 mmol) of benzyl 2,4-dihydroxybenzoate, 1.6 g (71%) of benzyl ester, melting point 123°–4° C., are obtained.

(c) 2-Hydroxy-4-(3,5-di-tert-butyl-4-hydroxybenzoylmethyloxy)benzoic acid 1.6 g (3.2 mmol) of the above ester, 260 mg of palladium on charcoal (10%) and 60 ml of dioxane are introduced into a reactor. The mixture is hydrogenated at room temperature and under a pressure of 7 bars for 2 h, the catalyst is filtered off and the filtrate is evaporated. The residue obtained is ground in hexane and dried and 1.1 g (86%) of the expected acid, melting point 166°–7° C., are obtained.

Example 38

2-Hydroxy-4-(5,6,7,8-tetrahydro-5,5,8,8-tetramethyl-2-naphthoylmethyloxy)benzaldehyde

12.4 g (0.04 mol) of 2-(2'-bromoaceto)-5,6,7,8-tetrahydro-5,5,8,8-tetramethylnaphthone, 5.5 g (0.04 mol) of 2,4-dihydroxybenzaldehyde, 5.5 g of potassium carbonate and 400 ml of methyl ethyl ketone are introduced into a round-bottomed flask. The mixture is heated to reflux for 1 h and filtered and the filtrate is evaporated. The residue obtained is purified by chromatography on a silica column and eluted with dichloromethane. After evaporation of the solvents, 9.9 g (67%) of the expected aldehyde, melting point 111°–2° C., are collected.

Example 39

1-(5,6,7,8-Tetrahydro-5,5,8,8-tetramethyl-2-naphthyl)-2-(3-hydroxy-4-methylphenoxy)ethanone

1 g (2.7 mmol) of 2-hydroxy-4-(5,6,7,8-tetrahydro-5,5,8,8-tetramethyl-2-naphthoylmethyloxy)benzaldehyde, 100 mg of palladium on charcoal (5%) and 50 ml of dioxane are introduced into a reactor. The mixture is hydrogenated at room temperature and under a pressure of 3 bars, the catalyst is filtered off and the filtrate is evaporated. The residue obtained is purified by chromatography on a silica column and eluted with a mixture of hexane and ethyl ether (70:30). After evaporation of the solvents, 600 mg of the expected product, melting point 144°–5° C., are collected.

Example 40

Methyl 2,6-dihydroxy-4-(5,6,7,8-tetrahydro-5,5,8,8-tetramethyl-2-naphthoylmethyloxy)benzoate

In a manner similar to Example 38, by reaction of 9.3 g (0.03 mol) of 2-(2'-bromoaceto)-5,6,7,8-tetrahydro-5,5,8,8-tetramethylnaphthone with 5.5 g (0.03 mol) of methyl 2,4,6-trihydroxybenzoate, 7.2 g (57%) of methyl ester, melting point 162°–3° C., are obtained.

Example 41

N-Ethyl-4-(3-tert-butyl-4-methoxybenzoyloxymethyl)benzamide

(a) 4-(3-tert-Butyl-4-methoxybenzoyloxymethyl)benzoyl chloride

In a manner similar to Example 1(c), starting with 3.4 g (0.01 mol) of 4-(3-tert-butyl-4-methoxybenzoyloxymethyl)benzoic acid prepared in Example 8, 3.6 g (100%) of crude acid chloride are obtained, which product is used in the next step of the synthesis without further treatment.

(b) N-Ethyl-4-(3-tert-butyl-4-methoxybenzoyloxymethyl)benzamide 12 ml of ethylamine and 50 ml of THF are introduced into a round-bottomed flask, a solution of 1.2 g (3.3 mmol) of the above acid chloride, dissolved in 30 ml of THF, is added dropwise and the mixture is stirred at room temperature for 4 h. This reaction medium is poured into water, the mixture is extracted with ethyl ether and the organic phase is separated after settling has taken place, dried over magnesium sulphate and evaporated. The residue obtained is ground in a mixture of hexane and ethyl ether (90:10) and filtered off. 740 mg (67%) of amide, melting point 107°–8° C., are collected.

Example 42

2-Hydroxy-4-(3-tert-butyl-4-methoxybenzoylmethyloxy)benzoic acid

(a) 3-tert-Butyl-4-methoxyacetophenone 22.6 g (0.1 mol) of 3-tert-butyl-4-methoxybenzoyl chloride and 30 ml of HMPA are introduced under a stream of nitrogen into a three-necked flask and 14 ml (0.1 mol) of tetramethyltin and 43 mg of benzyl(chloro)bis (triphenylphosphine)palladium(II) are added successively.

The mixture is heated to 80° C., for 4 h and stirred at room temperature for 12 h. The reaction medium is poured into water, the mixture is extracted with ethyl ether and the organic phase is separated after settling has taken place, dried over magnesium sulphate and evaporated. The residue obtained is purified by chromatography on a silica column and eluted with a mixture of hexane and dichloromethane (50:50). After evaporation of the solvents, 11.5 g (58%) of the expected product, melting point 68°–9° C., are collected.

(b) 2'-Bromo-3-tert-butyl-4-methoxyacetophenone

In a manner similar to Example 37(a), starting with 8.2 g (0.04 mol) of 3-tert-butyl-4-methoxyacetophenone, 8.7 g (76%) of the bromo derivative are obtain in the form of a slightly yellow oil.

(c) Benzyl 2-hydroxy-4-(3-tert-butyl-4-methoxybenzoylmethyloxy)benzoate

In a manner similar to Example 38, by reaction of 8.7 g (0.03 mol) of the above bromo compound with 7.5 g (0.03 mol) of benzyl 2,4-dihydroxybenzoate, 11 g (80%) of benzyl ester, melting point 98°–9° C., are obtained.

(d) 2-Hydroxy-4-(3-tert-butyl-4-methoxybenzoylmethyloxy)benzoic acid

In a manner similar to Example 37(c), starting with 2 g (4.4 mmol) of the above ester, 750 mg (48%) of the expected acid, melting point 170°–1° C., are obtained.

Example 43

Methyl 4-(3-tert-butyl-4-methoxybenzoyloxymethyl)benzoate 5 ml of methanol, 460 μl of triethylamine and 50 ml of THF are introduced into a round-bottomed flask. A solution of 1.2 g (3.3 mmol) of 4-(3-tert-butyl-4-methoxybenzoyloxymethyl)benzoyl chloride dissolved in 30 ml of THF is added dropwise and the mixture is stirred at room temperature for 4 h.

The mixture is evaporated to dryness, the residue is taken up with water and ethyl ether and the organic phase is separated after settling has taken place, dried over magnesium sulphate and evaporated. The residue obtained is purified by chromatography on silica and is eluted with a mixture of hexane and dichloromethane (50:50). After evaporation of the solvents, 580 mg (59%) of the expected ester, melting point 76°–7° C., are collected.

Example 44

N-Pyrrolidinyl-4-(3-tert-butyl-4-methoxybenzoyloxymethyl)benzamide

760 μl (5.5 mmol) of triethylamine, 450 μl (5.5 mmol) of pyrrolidine and 50 ml of THF are introduced into a round-bottomed flask. 1.8 g (5 mmol) of 4-(3-tert-butyl-4-methoxybenzoyloxymethyl)benzoyl chloride, dissolved in 50 ml of THF, are added dropwise and the mixture is stirred at room temperature for 4 h. The reaction medium is poured into water, the mixture is extracted with ethyl ether and the organic phase is separated after settling has taken place, dried over magnesium sulphate and evaporated.

The residue is purified by chromatography on a silica column and eluted with a mixture of dichloromethane and ethyl ether (90:10). After evaporation of the solvents, 1.4 g (73%) of the expected amide are collected in the form of an oil.

Example 45

4-(3-tert-Butyl-4-methoxybenzoyloxymethyl)benzaldehyde

(a) Methyl 4-(1,3-dioxolanyl)benzoate 8.2 g (0.05 mol) of methyl 4-formylbenzoate, 25 ml of ethylene glycol, 3.5 g of $ZnCl_2$ and 200 ml of xylene are introduced into a round-bottomed flask. The mixture is heated to reflux and the water formed is separated after settling has taken place, the organic phase is evaporated to dryness, the reaction medium is poured into water, the mixture is extracted with ethyl ether and the organic phase is separated after settling has taken place, dried over magnesium sulphate and evaporated. 10.4 g (100%) of the expected product are collected in the form of a colorless oil.

(b) 4-(1,3-Dioxolanyl)benzenemethanol 1.9 g (0.05 mol) of lithium aluminium hydride and 100 ml of THF are introduced into a three-necked flask. A solution of 10.4 g (0.05 mol) of the above methyl ester dissolved in 100 ml of THF is added dropwise under nitrogen and the mixture is heated to reflux for 4 h. It is hydrolyzed by adding 3.6 ml of an aqueous solution of sodium potassium tartrate, the salt is filtered off and the filtrate is evaporated. 8 g (90%) of the expected alcohol are collected in the form of a colorless oil.

(c) 4-Hydroxymethylbenzaldehyde 7.9 g (44 mmol) of the above alcohol and 100 ml of THF are introduced into a round-bottomed flask, 20 ml of hydrochloric acid (1N) are added and the mixture is heated to reflux for 4 h. The reaction medium is evaporated to dryness, the residue is taken up with ethyl ether and saturated sodium bicarbonate solution and the organic phase is separated after settling has taken place, dried over magnesium sulphate and evaporated.

The residue obtained is purified by chromatography on silica and eluted with dichloromethane. After evaporation of the solvents, 4.9 g (83%) of the expected product are collected in the form of an oil.

(d) 4-(3-tert-Butyl-4-methoxybenzoyloxymethyl)benzaldehyde

In a manner similar to Example 1(d), by reaction of 7.6 g (34 mmol) of 3-tert-butyl-4-methoxybenzoyl chloride with 4.6 g (34 mmol) of 4-hydroxymethylbenzaldehyde, 5.6 g (51%) of the expected aldehyde, melting point 75°–6° C., are obtained.

Example 46

4-(3-tert-Butyl-4-methoxybenzoyloxymethyl)benzenemethanol 1.6 g (5 mmol) of the aldehyde obtained in Example 45, 50 ml of THF and 50 ml of methanol are introduced into a round-bottomed flask. 100 mg (2.5 mmol) of sodium borohydride are added in small portions and the mixture is stirred at room temperature for 4 h. The reaction medium is poured into water, the mixture is extracted with ethyl ether and the organic phase is separated after settling has taken place, dried over magnesium sulphate and evaporated.

The residue obtained is ground in hexane and ether (80:20), filtered off and dried. 1.3 g (81%) of the expected alcohol, melting point 84°–5° C., are collected.

Example 47

4-(3-tert-Butyl-4-methoxybenzoyloxymethyl)benzenemethyl acetate 650 mg (2 mmol) of the alcohol obtained in Example 49, 320 μl (4 mmol) of pyridine and 50 ml of THF are introduced into a round-bottomed flask. A solution of 280 μl (4 mmol) of acetyl chloride in 20 ml of THF is added dropwise and the mixture is stirred at room temperature for 5 h. The reaction medium is poured into water, the mixture is extracted with ethyl ether and the organic phase is separated after settling has taken place, dried over magnesium sulphate and evaporated. The residue-obtained is purified by chromatography on a silica column and eluted with a mixture of ethyl ether and hexane (30:70). After evaporation of the solvents, 600 mg (81%) of the expected acetate are collected in the form of a colorless oil.

Example 48

4-(3-tert-Butyl-4-methoxybenzoyloxymethyl)phenol 1.24 g (0.01 mol) of 4-hydroxybenzenemethanol, 1 ml (0.01 mol) of pyridine and 50 ml of THF are introduced into a round-bottomed flask. While cooling in an icebath, a solution of 2.2 g (0.01 mol) of 3-tert-butyl-4-methoxybenzoyl chloride in 50 ml of THF is introduced dropwise and the mixture is stirred at room temperature for 24 h. The reaction medium is poured into water, the mixture is extracted with ethyl ether and the organic phase is separated after settling has taken place, dried over magnesium sulphate and evaporated. The residue obtained is purified by chromatography on a silica column and eluted with a mixture of dichloromethane and ethyl ether (97:3).

After evaporation of the solvents, 1.8 g (58%) of phenol, melting point 112°–3° C., are collected.

Example 49

4-(3-tert-Butyl-4-hydroxybenzoyloxymethyl)benzoic acid (a) Allyl 4-[3-tert-butyl-4-(tert-butyldimethylsilyloxy)benzoyloxymethyl]benzoate In a manner similar to Example 1(d), by reaction of 4.9 g (15 mmol) of 3-tert-butyl-4-(tert-butyldimethylsilyloxy)benzoyl chloride with 2.9 g (15 mmol) of allyl 4-hydroxymethylbenzoate, 4.1 g (60%) of the allyl ester are obtained in the form of a slightly yellow oil.

(b) 4-[3-tert-Butyl-4-(tert-butyldimethylsilyloxy)benzoyloxymethyl]benzoic acid

In a manner similar to Example 3(c), starting with 4 g (8.8 mmol) of the above allyl ester, 1.5 g (41%) of acid, melting point 152°–3° C., are obtained.

(c) 4-(3-tert-Butyl-4-hydroxybenzoyloxymethyl)benzoic acid 1.5 g (3.6 mmol) of the above acid and 75 ml of THF are introduced into a round-bottomed flask. 1.1 ml of a solution of tetrabutylammonium fluoride in THF (1M) are added dropwise under a stream of nitrogen and the mixture is stirred at room temperature for 1 h.

The reaction medium is evaporated to dryness, the residue is taken up with water and ethyl ether and the organic phase is separated after settling has taken place, dried over magnesium sulphate and evaporated.

The residue obtained is ground in hexane, filtered off and dried and 1 g (84%) of the expected acid, melting point 221°–2° C., is collected.

Example 50

5-(3-tert-Butyl-4-methoxybenzoyloxymethyl)-2-thiophenecarboxylic acid (a) Allyl 5-(3-tert-butyl-4-methoxybenzoyloxymethyl)-2-thiophenecarboxylate In a manner similar to Example 1(d), by reaction of 1.6 g (7 mmol) of 3-tert-butyl-4-methoxybenzoyl chloride with 1.4 g (7 mmol) of allyl 5-hydroxymethyl-2-thiophenecarboxylate, 1.5 g (55%) of allyl ester are obtained in the form of a slightly yellow oil.

(b) 5-(3-tert-Butyl-4-methoxybenzoyloxymethyl)-2-thiophenecarboxylic acid

In a manner similar to Example 3(c), starting with 1.5 g (4 mmol) of the above allyl ester, 930 mg (69%) of the expected acid, melting point 187°–8° C., are obtained.

Example 51

4-(3-tert-Butyl-4-isopropyloxybenzoyloxymethyl)benzoic acid (a) Benzyl 3-tert-Butyl-4-isopropyloxybenzoate 5.7 g (0.02 mol) of benzyl 3-tert-butyl-4-hydroxybenzoate, 7 g (0.05 mol) of finely ground potassium carbonate, 4 ml (0.04 mol) of 2-iodopropane and 100 ml of methyl ethyl ketone are introduced under nitrogen into a three-necked flask. The mixture is heated to reflux for 24 h, the inorganic matter is filtered off and the filtrate is evaporated. The residue is taken up with ethyl ether and water and the organic phase is separated after settling has taken place, dried over magnesium sulphate and evaporated.

The residue obtained is purified by chromatography on silica and eluted with dichloromethane, and 6.1 g (94%) of the expected benzyl ester are collected in the form of a yellow oil.

(b) 3-tert-Butyl-4-isopropyloxybenzoic acid

In a manner similar to Example 2(d), starting with 6.1 g (19 mmol) of the above benzyl ester, 3.8 g (86%) of the expected acid, melting point 178°–9° C., are obtained.

(c) 3-tert-Butyl-4-isopropyloxybenzoyl chloride

In a manner similar to Example 2(b), starting with 3.8 g (16 mmol) of 3-tert-butyl-4-isopropyloxybenzoic acid, 4.1 g (100%) of crude acid chloride are obtained, which product is used for the next step of the synthesis without further treatment.

(d) Allyl 4-(3-tert-butyl-4-isopropyloxybenzoyloxymethyl)benzoate

In a manner similar to Example 1(d), by reaction of 4.1 g (16 mmol) of 3-tert-butyl-4-isopropyloxybenzoyl chloride with 3.1 g (16 mmol) of allyl 4-hydroxymethylbenzoate, 5.1 g (77%) of allyl ester, melting point 63°–4° C., are obtained.

(e) 4-(3-tert-Butyl-4-isopropyloxybenzoyloxymethyl)benzoic acid

In a manner similar to Example 3(c), starting with 5.1 g (12 mmol) of the above allyl ester, 2.4 g (52%) of the expected acid, melting point 186°–7° C., are obtained.

Example 52

Allyl 4-(3,5-di-tert-butyl-4-hydroxybenzoyloxymethyl)benzoate

In a manner similar to Example 1(d), by reaction of 7.7 g (28.6 mmol) of 3,5-di-tert-butyl-4-hydroxybenzoyl chloride with 5.5 g (28.6 mmol) of allyl 4-hydroxymethylbenzoate, 4.1 g (34%) of the expected allyl ester, melting point 100°–1° C., are obtained.

Example 53

2-Hydroxy-4-(3-tert-butyl-4-methoxybenzoyloxymethyl)benzoic acid (a) Methyl 4-hydroxymethyl-2-hydroxybenzoate In a manner similar to Example 5(b), starting with 3.6 g (0.02 mol) of methyl 4-formyl-2-hydroxybenzoate, 3.7 g (100%) of the expected alcohol, melting point 77°–8° C., are obtained.

(b) 4-Hydroxymethyl-2-hydroxybenzoic acid

In a manner similar to example 12(b), starting with 3.7 g (0.02 mol) of methyl 4-hydroxymethyl-2-hydroxybenzoate, 3 g (80%) of the expected acid, melting point 179°–80° C., are obtained.

(c) Allyl 4-hydroxymethyl-2-hydroxybenzoate

In a manner similar to Example 7(a), starting with 3 g (18 mmol) of the above acid, 3 g (82%) of allyl ester, melting point 59°–60° C., are obtained.

(d) Allyl 2-hydroxy-4-(3-tert-butyl-4-methoxybenzoyloxymethyl)benzoate

In a manner similar to Example 1(d), by reaction of 2.4 g (10.5 mmol) of 3-tert-butyl-4-methoxybenzoyl chloride with 2.2 g (10.5 mmol) of allyl 4-hydroxymethyl-2-hydroxybenzoate, 2.5 g (61%) of the expected allyl ester are obtained in the form of a slightly yellow oil.

(e) 2-Hydroxy-4-(3-tert-butyl-4-methoxybenzoyloxymethyl)benzoic acid

In a manner similar to Example 3(c), starting with 2.3 g (6 mmol) of the above allyl ester, 595 mg (28%) of the expected acid, melting point 150°–1° C., are obtained.

Example 54

N-Morpholinyl-2-hydroxy-4-(5,6,7,8-tetrahydro-5,5,8,8-tetramethyl-2-naphthoylmethyloxy)benzamide

(a) 2-Hydroxy-4-(5,6,7,8-tetrahydro-5,5,8,8-tetramethyl-2-naphthoylmethyloxy)benzoyl chloride 5.36 ml (73.7 mmol) of thionyl chloride are added dropwise to a suspension, heated to 80° C., of 25.5 g (67 mmol) of the acid obtained in Example 32 in 255 ml of toluene and 2.55 ml of DMF.

The mixture is stirred for 1 h at 80° C., and the solvent is then evaporated off under vacuum. The acid chloride obtained (26.7 g), dissolved in THF, is used directly for the preparation of amides.

(b) N-Morpholinyl-2-hydroxy-4-(5,6,7,8-tetrahydro-5,5,8,8-tetramethyl-2-naphthoylmethyloxy)benzamide A solution of 8.9 g (22 mmol) of the above acid chloride in 90 ml of THF is added dropwise to a mixture of 17.5 g (200 mmol) of morpholine and 90 ml of THF at room temperature. The mixture is stirred for a further 1 h and is then poured into water and the resulting mixture is acidified to pH 5–6 with HCl.

The mixture is extracted with ethyl acetate and the organic phase is washed with water and dried over sodium sulphate. On evaporation, 12 g of crude amide are obtained, which product is purified by chromatography on a silica column and eluted with a mixture of ethyl acetate and hexane (45:55). 8.55 g (85.5%) of a white product, melting point 166°–7° C., are collected.

Example 55

2-Hydroxy-4-(5,6,7,8-tetrahydro-5,5,8,8-tetramethyl-2-naphthoylmethyloxy)benzamide A solution of 8.9 g (22 mmol) of the acid chloride described in Example 54(a) in 90 ml of THF is added dropwise to 100 ml of a saturated solution of ammonia in THF at room temperature. The mixture is stirred for a further 1 h and is then poured into water and the resulting mixture is acidified to pH 5–6 with HCl.

The mixture is extracted with ethyl acetate and the organic phase is washed with water and dried over sodium sulphate. The crude product obtained on evaporation is chromatographed on a silica column and eluted with a mixture of ethyl acetate and hexane (40:60). 6.94 g (82.6%) of cream-white powder, melting point 196°–7° C., are collected.

Example 56

N-Piperridyl-2-hydroxy-4-(5,6,7,8-tetrahydro-5,5,8,8-tetramethyl-2-naphthoylmethyloxy)benzamide A solution of 6 g (15 mmol) of the acid chloride described in Example 54(a) in 60 ml of THF is added dropwise to a mixture of 4.44 ml (45 mmol) of piperidine and 60 ml of THF at room temperature. The mixture is stirred for a further 2 h and is then poured into water and the resulting mixture is acidified to pH 6–7 with HCl.

The mixture is extracted with ethyl acetate and the organic phase is washed with water and dried over sodium sulphate. The crude product obtained (7 g) is crystallized with a mixture of ethyl acetate and hexane (30:70). 5.04 g (75.2%) of cream-white powder, melting point 120°–4° C., are collected.

Example 57

N-Ethyl-2-hydroxy-4-(5,6,7,8-tetrahydro-5,5,8,8-tetramethyl-2-naphthoylmethyloxy)benzamide A solution of 8.9 g (22 mmol) of the acid chloride described in Example 54(a) in 90 ml of THF is added dropwise to 67 ml of a 3N solution of ethylamine in ethanol at room temperature. The mixture is stirred for 2 h and then poured into water and the resulting mixture is extracted with ethyl acetate after acidification with HCl to pH 5–6.

The organic phase is washed with water and then dried over sodium sulphate. The crude product obtained on evaporation under vacuum is chromatographed on a silica column and eluted with a mixture of ethyl acetate and hexane (20:80). 970 mg of a pale yellow powder, melting point 134° C., are collected.

Example 58

2-Hydroxy-4-[3-(1-adamantyl)-4-methoxybenzoylmethyloxy]benzoic acid

(a) 3-(1-Adamantyl)-4-methoxyphenylethanone 15.75 g (0.055 mol) of 3-(1-adamantyl)-4-methoxybenzoic acid, dissolved in 150 ml of toluene, are treated with 7.3 ml of thionyl chloride and heated to 100° C., for 3 h 30 min. The reaction medium is evaporated to dryness and 30 ml of hexamethylphosphoramide, 8 ml (0.0575 mol) of tetramethyltin and 22 mg of benzylbis(triphenylphosphine)palladium(II) chloride are then added under nitrogen to this evaporation residue. The reaction medium is heated to 65° C., for 30 min and is then left stirring at room temperature overnight. The reaction medium is poured into water and the mixture is extracted with ether. After chromatography on silica, 10.47 g (71%) of the expected derivative, melting point 138°–140° C., are isolated in the dichloromethane/hexane (60:40) eluent.

(b) [3-(1-Adamantyl)-4-methoxyphenyl]-2-bromoethanone 5.63 g (19.8 mmol) of the ketone obtained in Example 58(a), dissolved in 30 ml of dioxane and 30 ml of ethyl ether, are treated with 1 ml of bromine (19.8 mmol) dissolved in 15 ml of dichloromethane. The reaction medium is left stirring for 30 min at room temperature and is then poured into 200 ml of water and the mixture is extracted with 700 ml of ethyl ether. After washing and drying of the organic phase, 6.7 g (93%) of the expected derivative, melting point 140°–1° C., are isolated.

(c) Benzyl 2-hydroxy-4-[3-(1-adamantyl)-4-methoxybenzoylmethyloxy]benzoate 4.90 g (20 mmol) of benzyl 2,4-dihydroxybenzoate are treated with 605 mg of sodium hydride (80% in oil) in 50 ml of DMF. 7.29 g (20 mmol) of the bromo derivative obtained in the preceding example, dissolved in 100 ml of DMF, are then added dropwise and the mixture is left to react with stirring for 2 h at room temperature. After the usual treatment, 7.39 g (70%) of the expected derivative, melting point 129° C., are isolated.

(d) 2-Hydroxy-4-[3-(1-adamantyl)-4-methoxybenzoylmethyloxy]benzoic acid 3.68 g (6.98 mmol) of the ester obtained in Example 58(c), in 50 ml of dioxane and 0.5 ml of acetic acid, are hydrogenated in the presence of 57 mg of palladium on charcoal (10%) at 40° C., under a pressure of 7 bars of hydrogen for 3 h 30 min. After treatment and recrystallization in a water/ethanol mixture, 2.32 g (76%) of the expected derivative, melting point 225°–6° C., are isolated.

Example 59

(−)-4-{[1-(5,6,7,8-Tetrahydro-5,5,8,8-tetramethyl-2-naphthyl)ethyloxy]carbonyl}benzoic acid (a) (+)-1-(5,6,7,8-tetrahydro-5,5,8,8-tetramethyl-2-naphthyl)ethanol 6 g of (±)-acetoxy-1-(5,6,7,8-tetrahydro-5,5,8,8-tetramethyl-2-naphthyl)ethane, suspended in a mixture of 100 ml of phosphate buffer (0.3M, pH 7) and 1 ml of chloroform, are treated with 0.87 g of Amano P30 lipase with stirring at 40° C. for 3 days. 2.06 g (88%) of the expected product, melting point 61°–2° C. ($\alpha_D$=+27°; c=1, ethanol) and 2.2 g (73%) of acetoxy-1-(5,6,7,8-tetrahydro-5,5,8,8-tetramethyl-2-naphthyl)ethane are isolated.

(b) Allyl (−)-4-{[1-(5,6,7,8-tetrahydro-5,5,8,8-tetramethyl-2-naphthyl)ethyloxy]carbonyl}benzoate 1.54 g (7.44 mmol) of dicyclohexylcarbodiimide and 0.91 g of 4-dimethylaminopyridine are added to a solution of 1.73 g (7.44 mmol) of (+)-1-(5,6,7,8-tetrahydro-5,5,8,8-tetramethyl-2-naphthyl)ethyl alcohol and 1.54 g (7.44 mmol) of allyl monoterephthalate in 50 ml of THF. The reaction medium is left stirring at room temperature for 3 h. After treatment and chromatography on silica in dichloromethane, 2.42 g (77%) of the expected derivative are isolated in the form of a colorless oil (Rf=0.46; dichloromethane/hexane, 50:50).

(c) (−)-4-{[1-(5,6,7,8-tetrahydro-5,5,8,8-tetramethyl-2-naphthyl)ethyloxy]carbonyl}benzoic acid A solution of 2.40 g (5.71 mmol) of the ester obtained in Example 59(b) in 30 ml of THF is treated with 340 mg of tetrakis(triphenylphosphine)palladium(O) and 5 ml of morpholine under the preparation conditions of Example 24(b), to yield 1.94 g (89%) of the expected derivative, melting point 138° C. ($\alpha_D$=−53.2°; c=1, ethanol).

Example 60

(+)-4-{[1-(5,6,7,8-tetrahydro-5,5,8,8-tetramethyl-2-naphthyl)ethyloxy]carbonyl}benzoic acid (a) (−)-1-(5,6,7,8-tetrahydro-5,5,8,8-tetramethyl-2-naphthyl)ethanol 2.2 g (8 mmol), obtained in Example 59(a), of acetoxy-1-(5,6,7,8-tetrahydro-5,5,8,8-tetramethyl-2-naphthyl)ethane, dissolved in 20 ml of methanol, are treated with 1.6 g of sodium hydroxide and left stirring for 24 h at room temperature. After evaporation and acidification with 1N HCl, the precipitate is extracted with ethyl ether to yield 1.75 g (93%) of the expected alcohol, melting point 61°–2° C. ($\alpha_D$=−27.2°; c=1, ethanol).

(b) Allyl (+)-4-{[1-(5,6,7,8-tetrahydro-5,5,8,8-tetramethyl-2-naphthyl)ethyloxy]carbonyl}benzoate 1.69 g (7.27 mmol) of the alcohol obtained in Example 60(a) is condensed with 1.5 g of allyl monoterephthalate under the conditions described in Example 22(a), to yield, after treatment and chromatography on silica, to 2.54 g (83%) of the expected ester in the form of a colorless oil. Rf=0.46 (dichloromethane/hexane, 50:50).

(c) (+)-4-{[1-(5,6,7,8-tetrahydro-5,5,8,8-tetramethyl-2-naphthyl)ethyloxy]carbonyl}benzoic acid 2.53 g (6 mmol) of the ester obtained in Example 60(b) are treated under the conditions described for the preparation of Example 22(b), to yield 1.72 g (75%) of the expected derivative, melting point 138° C. ($\alpha_D$=+52.1; c=1, ethanol).

FORMULATION EXAMPLES

A. FOR ORAL ADMINISTRATION (a) 0.2 g tablet

| | |
|---|---|
| 4-(5,6,7,8-Tetrahydro-5,5,8,8-tetramethyl-2-naphthylmethyloxycarbonyl)benzoic acid | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

In this example, 4-(5,6,7,8-tetrahydro-5,5,8,8-tetramethyl-2-naphthylmethyloxycarbonyl)benzoic acid may be replaced by 4-(5,6,7,8-tetrahydro-5,5,8,8-tetramethyl-2-naphthoyloxymethyl)benzoic acid.

(b) Suspension to be taken by mouth, in 5 ml ampoules

| | |
|---|---|
| 4-(5,6,7,8-Tetrahydro-5,5,8,8-tetramethyl-2-naphthyloxy-carboxamido)benzoic acid | 0.001 g |
| Glycerol | 0.500 g |
| Sorbitol, 70% | 0.500 g |
| Sodium saccharinate | 0.010 g |
| Methyl para-hydroxybenzoate | 0.040 g |
| Flavoring qs | |
| Purified water qs | 5 ml |

In this example, 4-(5,6,7,8-tetrahydro-5,5,8,8-tetramethyl-2-naphthyloxycarboxamido)benzoic acid may be replaced by 4-(5,6,7,8-tetrahydro-5,5,8,8-tetramethyl-2-naphthylacetamido)benzoic acid.

(c) 0.8 g tablet

| | |
|---|---|
| 4-[1-(5,6,7,8-tetrahydro-5,5,8,8-tetramethyl-2-naphthoyloxy)ethyl]benzoic acid | 0.500 g |
| Pregelatinized starch | 0.100 g |
| Microcrystalline cellulose | 0.115 g |
| Lactose | 0.075 g |
| Magnesium stearate | 0.010 g |

In this example, 4-[1-(5,6,7,8-tetrahydro-5,5,8,8-tetramethyl-2-naphthoyloxy)ethyl]benzoic acid maybe replaced by 4-(5,6,7,8-tetrahydro-5,5,8,8-tetramethyl-2-naphthoylmethyloxy)benzoic acid.

(d) Suspension to be taken by mouth, in 10 ml ampoules

| | |
|---|---|
| 4-(5,6,7,8-Tetrahydro-5,5,8,8-tetramethyl-2-naphthoylform- amido)benzoic acid | 0.05 g |
| Glycerol | 1.000 g |
| Sorbitol, 70% | 1.000 g |
| Sodium saccharinate | 0.010 g |
| Methyl para-hydroxybenzoate | 0.080 g |
| Flavoring qs | |
| Purified water qs | 10 ml |

In this example, 4-(5,6,7,8-tetrahydro-5,5,8,8-tetramethyl-2-naphthoylformamido)benzoic acid may be replaced by 4-(α-hydroxy-5,6,7,8-tetrahydro-5,5,8,8-tetramethyl-2-naphthylacetamido)benzoic acid or by 2-hydroxy-4-(5,6,7,8-tetrahydro-5,5,8,8-tetramethyl-2-naphthoylmethyloxy)benzoic acid.

B. FOR TOPICAL ADMINISTRATION (a) Ointment

| | |
|---|---|
| 4-(5,6,7,8-Tetrahydro-5,5,8,8-tetramethyl-2-naphthylacet- oxy)benzoic acid | 0.020 g |
| Isopropyl myristate | 81.700 g |
| Light liquid paraffin | 9.100 g |
| Silica sold by the company DEGUSSA under the name "Aerosil 200" | 9.180 g |

In this example, 4-(5,6,7,8-tetrahydro-5,5,8,8-tetramethyl-2-naphthylacetoxy)benzoic acid maybe replaced by 4-(5,6,7,8-tetrahydro-5,5,8,8-tetramethyl-2-naphthyloxycarboxamido)benzoic acid.

(b) Ointment

| | |
|---|---|
| 4-(5,6,7,8-Tetrahydro-5,5,8,8-tetramethyl-2-naphthoylthio- methyl)benzoic acid | 0.300 g |
| White vaseline codex qs | 100 g |

In this example, 4-(5,6,7,8-tetrahydro-5,5,8,8-tetramethyl-2-naphthoylthiomethyl)benzoic acid may be replaced by 4-(5,6,7,8-tetrahydro-5,5,8,8-tetramethyl-2-naphthylacetamido)benzoic acid.

(c) Nonionic water-in-oil cream

| | |
|---|---|
| 4-(α-Methylene-5,6,7,8-tetrahydro-5,5,8,8-tetramethyl-2- naphthylacetoxy)benzoic acid | 0.100 g |
| Mixture of refined waxes, oils and emulsive lanolin alcohols, sold by the company BDF under the name "Eucerin, anhydrous" | 39.900 g |
| Methyl para-hydroxybenzoate | 0.075 g |
| Propyl para-hydroxybenzoate | 0.075 g |
| Sterile demineralized water qs | 100 g |

In this example, 4-(α-methylene-5,6,7,8-tetrahydro-5,5,8,8-tetramethyl-2-naphthylacetoxy)benzoic acid may be replaced by 4-[1-(5,6,7,8-tetrahydro-5,5,8,8-tetramethyl-2-naphthoyloxy)ethyl]benzoic acid.

(d) Lotion

| | |
|---|---|
| 4-(3-tert-Butyl-4-methoxybenzoyloxymethyl)benzoic acid | 0.100 g |
| Polyethylene glycol (PEG 400) | 69.900 g |
| Ethanol, 95% | 30.000 g |

In this example, 4-(5,6,7,8-tetrahydro-5,5,8,8-tetramethyl-2-naphthyloxyacetyl)benzoic acid may be replaced by 4-(5,6,7,8-tetrahydro-5,5,8,8-tetramethyl-2-naphthylmethyloxycarbonyl)benzoic acid.

(e) Hydrophobic ointment

| | |
|---|---|
| 4-(5,6,7,8-Tetrahydro-5,5,8,8-tetramethyl-2-naphthoyloxy- methyl)benzoic acid | 0.300 g |
| Isopropyl myristate | 36.400 g |
| Silicone oil sold by the company Rhône Poulenc under the name "Rhodorsil 47 V 300" | 36.400 g |
| Beeswax | 13.600 g |
| Silicone oil sold by the company Goldschmidt under the name "Abil 300.000 cst" qs | 100 g |

In this example, 4-(5,6,7,8-tetrahydro-5,5,8,8-tetramethyl-2-naphthoyloxymethyl)benzoic acid may be replaced by 4-(3,5-di-tert-butyl-4-hydroxybenzoyloxymethyl)benzoic acid.

(f) Nonionic oil-in-water cream

| | |
|---|---|
| 5-(5,6,7,8-Tetrahydro-5,5,8,8-tetramethyl-2-naphthoyloxy- methyl)-2-thiophenecarboxylic acid | 0.500 g |
| Cetyl alcohol | 4.000 g |
| Glyceryl monostearate | 2.500 g |
| PEG 50 stearate | 2.500 g |
| Shea butter | 9.200 g |
| Propylene glycol | 2.000 g |
| Methyl para-hydroxybenzoate | 0.075 g |
| Propyl para-hydroxybenzoate | 0.075 g |
| Sterile demineralized water qs | 100 g |

We claim:

1. A di(aromatic) compound having the formula $$Ar-X-\underset{Z}{\overset{R_2}{\diagdown}}-R_1$$

wherein
Ar represents (with $(CH_2)_n$ bridge on benzene ring)

wherein n=1 or 2 or (benzene ring with $R_3$, $R_4$, $R_5$ substituents)

wherein $R_3$ and $R_5$ represent hydrogen, OH, alkoxy having 1–6 carbon atoms, α-branched alkyl having from 3–12 carbon atoms, α,α-branched alkyl having from 4–12 carbon atoms, cycloalkyl having 3–12 carbon atoms, or mono- or polycyclic cycloalkyl having 5–12 carbon atoms in which the carbon having the free valence is trisubstituted, $R_4$ represents alkoxy having 1–6 carbon atoms, α-branched alkyl having 3–12 carbon atoms, α,α-branched alkyl having 4–12 carbon atoms, cycloalkyl having 3–12 carbon atoms, mono- or polycyclic cycloalkyl having 5–12 carbon atoms in which the carbon having the free valence is trisubstituted, monohydroxyalkyl, polyhydroxyalkyl, fluorine, chlorine, SH, SR$_6$, SOR$_6$, SO$_2$R$_6$, alkenyl having 2–6 carbon atoms or alkenyloxy having 2 to 6 carbon atoms, R$_6$ represents lower alkyl, R$_1$ represents —COR$_7$ R$_7$ represents hydrogen, OH, —OR$_{10}$, —N(r'r"), monohydroxyalkyl, polyhydroxyalkyl or a sugar residue, R$_{10}$ represents alkyl having 1–12 carbon atoms or alkenyl having 2–12 carbon atoms, r' and r", each independently, represent hydrogen, lower alkyl, aryl, aralkyl, an amino acid residue, a sugar residue, an amino sugar residue or a heterocycle, or r' and r" taken together form a heterocycle selected from the group consisting of piperidino, morpholino, pyrrolidino, piperazino and piperazino radical substituted at the 4-position with a C$_1$-C$_6$ alkyl or a mono- or polyhydroxyalkyl radical, R$_2$ represents hydrogen, OH, lower alkyl, alkoxy having 1–6 carbon atoms, fluorine, chlorine, CF$_3$, COR$_7$, CH$_2$OH or CH$_2$OR$_6$ wherein R$_6$ has the meaning given above, Z represents an oxygen atom, a sulphur atom, —CH=CR$_{11}$—, —N=CH— or —N=CR$_6$— wherein R$_6$ has the meaning given above, R$_{11}$ represents hydrogen, OH, lower alkyl, alkoxy having 1–6 carbon atoms, fluorine, chlorine or CF$_3$, X represents a divalent radical which can be read from left to right or vice versa and has the formula

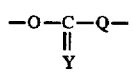

wherein

Q represents oxygen or —NR'—,

R' represents a hydrogen atom or a —CH$_3$ radical and

Y represents oxygen or, alternatively Y represents sulphur when Q represents —NR' and the salts thereof when R$_1$ represents a carboxylic acid function.

2. The di(aromatic) compound of claim 1 selected from the group consisting of 4-(5,6,7,8-tetrahydro-5,5,8,8-tetramethyl-2-naphthyloxycarboxamido)benzoic acid, 4-[5,6,7,8-tetrahydro-5,5,8,8-tetramethyl-2-naphthyl(carbonyldioxy)]benzoic acid, 4-[3-(1-adamantyl)-4-methoxyphenoxycarboxamido]benzoic acid, and 4-[3-(1-adamantyl)-4-methoxyphenyl(carbonyldioxy)]benzoic acid.

3. The di(aromatic) compound of claim 1 in the form of an alkali metal salt, an alkaline earth metal salt, a zinc salt or a salt of an organic amine.

4. The di(aromatic) compound of claim 1 wherein said lower alkyl has 1–6 carbon atoms.

5. The di(aromatic) compound of claim 1 wherein said lower alkyl is selected from the group consisting of methyl, ethyl, isopropyl, butyl and tert.butyl.

6. The di(aromatic) compound of claim 1 wherein said alkoxy having 1–6 carbon atoms is selected from the group consisting of methoxy, ethoxy, isopropoxy and butoxy.

7. The di(aromatic) compound of claim 1 wherein said α-substituted alkyl having 3–12 carbon atoms is selected from the group consisting of isopropyl, 1-methylpropyl and 1-ethylpropyl.

8. The di(aromatic) compound of claim 1 wherein said α,α-disubstituted alkyl having 4–12 carbon atoms is selected from the group consisting of tert.butyl, 1,1-dimethylpropyl, 1-methyl-1-ethylpropyl, 1-methyl-1-ethylhexyl and 1,1-dimethyldecyl.

9. The di(aromatic) compound of claim 1 wherein said monohydroxyalkyl is 2-hydroxyethyl, 2-hydroxypropyl or 3-hydroxypropyl.

10. The di(aromatic) compound of claim 1 wherein said polyhydroxyalkyl has 3–6 carbon atoms and 2–5 hydroxyl groups.

11. The di(aromatic) compound of claim 1 wherein said polyhydroxyalkyl is selected from the group consisting of 2,3-dihydroxypropyl, 2,3,4-trihydroxybutyl, 2,3,4,5-tetrahydroxypentyl and pentaerythritolol.

12. The di(aromatic) compound of claim 1 wherein said aryl is phenyl optionally substituted by at least one halogen, hydroxyl or nitro function.

13. The di(aromatic) compound of claim 1 wherein said aralkyl is benzyl or phenethyl, optionally substituted by at least one halogen, hydroxyl or nitro function.

14. The di(aromatic) compound of claim 1 wherein said mono- or polycyclic cycloalkyl having 5–12 carbon atoms in which the carbon having the free valence is trisubstituted is 1-methylcyclohexyl or 1-adamantyl.

15. A pharmaceutical composition comprising in a vehicle suitable for enteral, parenteral, topicular or ocular administration at least one compound of formula (I) of claim 1.

16. The pharmaceutical composition of claim 15 wherein said compound of formula (I) is present in an amount ranging from 0.0001 to 5 weight percent.

17. A method for the treatment of a dermatological, rheumatic, respiratory or ophthalmological condition of a person suffering from said condition, said method comprising administering to said person in an amount effective to treat said condition the pharmaceutical composition of claim 15.

18. A cosmetic composition for body and hair hygiene comprising, in a cosmetically acceptable vehicle at least one compound of formula (I) of claim 1.

19. The cosmetic composition of claim 18 wherein said compound of formula (I) is present in an amount ranging from 0.0001 to 1 weight percent.

20. The cosmetic composition of claim 18 wherein said compound of formula (I) is present in an amount ranging from 0.001 to 0.01 weight percent.

* * * * *